United States Patent [19]
Rosson

[11] Patent Number: 5,612,184
[45] Date of Patent: Mar. 18, 1997

[54] DEVICE FOR DETECTING MERCURY IN WATER

[75] Inventor: Reinhardt A. Rosson, Manitowoc, Wis.

[73] Assignee: Bio-Technical Resources L.P., Manitowoc, Wis.

[21] Appl. No.: 468,405

[22] Filed: Jun. 6, 1995

Related U.S. Application Data

[60] Division of Ser. No. 111,316, Aug. 23, 1993, which is a continuation-in-part of Ser. No. 737,951, Jul. 30, 1991, abandoned.

[51] Int. Cl.⁶ .................................................... C12Q 1/70
[52] U.S. Cl. ........................... 435/6; 435/172.3; 935/56; 935/59; 422/52; 422/82.08
[58] Field of Search ................... 435/5, 172.3, 6; 935/56, 59; 422/52, 79, 82.08

[56] References Cited

U.S. PATENT DOCUMENTS

| | | |
|---|---|---|
| 4,396,579 | 8/1983 | Schroeder et al. |
| 4,581,335 | 4/1986 | Baldwin . |
| 4,861,709 | 8/1989 | Ulitzur et al. |
| 4,863,689 | 9/1989 | Leong et al. |
| 4,954,318 | 9/1990 | Yafuso et al. |
| 4,968,613 | 11/1990 | Masuda et al. |
| 5,094,819 | 3/1992 | Yager et al. |

FOREIGN PATENT DOCUMENTS

| | | |
|---|---|---|
| 0496027 | 6/1991 | European Pat. Off. |
| 3902982 | 8/1990 | Germany . |
| 9004037 | 4/1990 | WIPO . |
| 9008836 | 8/1990 | WIPO . |
| 9215687 | 9/1992 | WIPO . |

OTHER PUBLICATIONS

T. Maniatis et al., Molecular Cloning, a Laboratory Manual, *Cold Spring Harbor, NY*, pp. 34–41, pp. 49–87, pp. 133–141, pp. 261–268, (1982).

Promega Protocol and Application Guide, 2nd Ed., Madison WI, 1991 pp. 1.3–1.105, 4.3–4.51, 5.3–5.90, 6.3–6.60, 10.6–10.68, 13.3–13.102, 14.5–14.34, 15.3–15.109, 17.3–17.42, A.1–H.

T.S. Hultman et al., Nuc. Acids Res., vol. 17, p. 4945, 1989.

F.S. Sanger, et al., Proc. Natl. Acad. Sci, USA, 74, 5463–5467 1977.

Meighnan and Szittner, J. Bacteriol., 174, 5371–5381, 1992.

Miyamoto et al., Nuc Acid Res., 16, 1551–1562, 1988.

Karp, M., Biochem and Bio Phys Research Communications 1007, 84–90, 1989.

Silverman, et al., Genetics of Bacterial Diversity, Academic Press, Inc. London, 71–86, 1989.

Stanley, et al. Journal of Biol. & Chem. vol. 5, 141–152, 1990.

Ultizor, et al., Methods on Enzymology, Academic Press, Inc. London, 264–274, 1986.

Kricka et al, Journal of Bioluminescience and Chemiluminescience vol. 7, 47 1992.

Bulrch A.A, Proc. Biochem, 17, 45–47, 1982.

S. Frackman, et al., J. Bacteriol, 172, 5767–5773, 1990.

Silver, et al, Ann Rev. Microbiol., 42, 717–743, 1988.

Silver, et al, Microbiol Rev. 56, 195–228, 1992.

Ross, et al, J. Balt., vol. 171, No. 7, 4009–4018 (Jul. 1989).

(List continued on next page.)

*Primary Examiner*—Paul B. Prebilic

[57] ABSTRACT

Devices for the detection of small quantities either of divalent inorganic mercury ion ($Hg^{2+}$) or of both $Hg^{2+}$ and monomethyl mercury in water are disclosed. These devices comprises a bioluminescence detecting means and a bioluminescent biosensory microorganism cells, that emit significant light only when exposed to either to $Hg^{2+}$ or to $Hg^{2+}$ or momomethyl mercury. Plasmid cassettes and host microorganisms containing such cassettes are also disclosed The plasmid cassettes comprises a lux gene operon complex from *Xenorhabdus luminescens*. The lux operon complex comprises luxC, luxD, luxA, luxB, and luxE genes but is free of (1) a promoter for the complex and (2) an inducible regulatory gene for the complex.

12 Claims, 18 Drawing Sheets

OTHER PUBLICATIONS

R. Szittner and E. Meighen, J. Biol. Chem., 265, 16581–16587, 1990.
Xi, et al, J. Bacteriol, 173, 1399–1405, 1991.
Burlage, et al, Journal of Bacteriology, 171, 4749–4757, 1990.
Carmiet, et al., J. Bacteriol, 169, 2165–2170, 1987.
Condee, et al, International Marine Brotech Conference, Baltimore, MD, Society for Industrial Microbiology, 1991.
Engebrecht, et al, Science, 227, 1345–1347, 1985.
Farinha, et al, J. Bacteriol, 172, 3496–3499, 1990.
King, et al, Science, 249, 778–781, 1990.
Meighen, E.A., Annual Reviews of Microbiology, 42, 151–176, 1988.
Nordeen, S.K., Bio-techniques, 6, 454–457, 1988.
Rogers, et al, Biosensors for Environmental Mentoring, vol. 7, 317–321, 1992.
Schmidt, etal, Applied and Environmental Microbiology, vol. 55, 2607–2612, 1989.
Ulitzur et al, Journal of Biol & Chem, 2, 95–99, 1988.
Bulich, A.A. in L.L. Marking, et al (ed) Aquatic Toxicology, 98–106, 1979.
Elnabarawy, et al, Toxicology Assessment an International Journal, 3, 361–370, 1988.
Griffin, et al. Proc National Acad. Science U.S.A., 84, 3112–3116, 1987.
Nucifora, et al, J. Bacteriol, 171, 4241–4247, 1989.
Park, et al, J. Bacteriol, 174, 2160–2171, 1992.
O'Halleran, et al Pro. National Academic Science, 56, 119–129, 1989.
Rattray, et al, Appl. Environmental Microbiology, 56, 3368–3374, 1990.
Abstract of patent WO-9010710 published Sep. 20, 1990.
Abstract of patent JP-02174697 dated Jul. 6, 1990.
Abstract of patent WO-9001542 dated Feb. 22, 1990.
Abstract of patent EP-353464-A dated Feb. 7, 1990.
Abstract of WO-9004053 dated Apr. 19, 1990.
Abstract of JP-2002363 dated Jan. 8, 1990.
Abstract of WO-8801646 dated Mar. 10, 1988.
Abstract of WO-8800617 dated Jan. 28, 1988.

pCGLS1
(X. luminescens lux clone)

pSD721
(P. lelognathi lun clone)

MONOMETHYL MERCURY CONCENTRATION (μM)

FIG. 15

```
  1 CTGCAGCCCG GTACCGAGCT CGAATTCTTC TTTAGAAATC TGCCGGTAAA
 51 AATTAGATTG CTATTCAATC TATTTCTATC GGTATTTGTG AAATAATACT
101 CAGGATAATA ATTTACATAA ATATTATCAC GCATTAGAGA AGAGCATGAC
151 TTTTTTAATT TAAACTTTTC ATTAACAAAT CTTGTTGATA TGAAAATTTT
201 CCTTTGCTAT TTAACAGAT ATTAAAACGG GAATAGGCGT TATATTGACG
251 ATCCATTCAG TTAGATTAAA AACCTTGAGC AGAAAATTTA TATTATTATC
301 ATAATTATGA CGAAAGTTAC AGGCCAGGAA CCACGTAGTC AGAATCTGAT
351 TTTCTATATA TTTGTTATTT ACATCGTCAT AACACAAAAA TATAAGAAGC
401 AAGTGTTGGT ACGACCAGTT CGCAAGTAAG TTAACGCACT TAGTGAATAC
451 CCATTAATGG ATGGCAATAT GACTAAAAAT TCATCATATC GCAGTGAATC
501 TTCCGA
```
SEQ. ID NO. 1

FIG. 16

```
  1 CTGCAGCCCG GGTACCGAGC TCGCGCCATT CAGGCTGCGC AACTGTTGGG
 51 GCAAATATGA CTAAAAAAAT TTCATTCATT ATTAACGGCC AGGTTGAAAT
101 CTTTCCCGAA AGTGATGATT TAGTGCAATC CATTAATTTT GGTGATAATA
151 GTGTTTACCT GCCAATATTG AATGACTCTC ATGTAAAAAA CATTATTGAT
201 TGTAATGGAA ATAACGAATT ACGGTTGCAT AACATTGTCA ATTTCTCTA
251 TACGGTAGGG CAAAGATGGA AAAATGAAGA ATACTCAAGA CGCAGGACAT
301 ACATTCGTGA CTTAAAAAAA TATATGGGAT ATTCAGAAGA AATGGCTAAG
351 CTAGAGGCCA ATTGGATATC TATGATTTTA TGTTCTAAGG CGGCCTTATG
401 ATGTTGATGA AATGACTTGG TTCTCGCCAT ATCATGGATG ATGCTCATCA
451 GGATGAAGTT ATGTTCGGCT TTCGAA
```
SEQ. ID NO. 2

FIG. 17b

```
          T A C G G T A G G G C A A A G A T G G A A A A A T G A A G A A T A C T C A A G A C G C A G G A C A T  Consensus #1
                    210                 220                 230                 240                 250
    251   T A C G G T A G G G C A A A G A T G G A A A A A T G A A G A A T A C T C A A G A C G C A G G A C A T  X. l. Hm (Taylor)
    202   T A C G G T A G G G C A A A G A T G G A A A A A T G A A G A A T A C T C A A G A C G C A G G A C A T  X. l. Hb (Meighen)
    202   T A C G G T A G G G C A A A G A T G G A T T G A A G A A T A C T C A A G A C G C A G G A C A T  X. l. Hw (Meighen)
    202   T A C G G T A G G G C A A A C G T T G G A A A A A T G A A G A A T A T T C A A G A C G C A G A C C A T  X. l. Hw (Xl)

A C A T T C G T G A - C T T A A A A A A A T A T A T G G G A T A T T C A G A A G A A A T G G C T A A  Consensus #1
                    260                 270                 280                 290                 300
          A C A T T C G T G A - C T T A A A A A A A T A T A T G G G A T A T T C A G A A G A A A T G G C T A A  X. l. Hm (Taylor)
          A C A T T C G T G A - C T T T A A A A A A T A T A T G G G A T A T T C A G A A G A A A T G G C T A A  X. l. Hb (Meighen)
          A C A T T C G T G A T C T T A A A A A A A G A T A T G G G A T A T T C A G A A G A A A T G G C T A A  X. l. Hw (Meighen)
          A T A T T C G T G A T C T C T A A A A A A G A T A T G G G A T A T T T C A G A A G A A - T T G G C T A A  X. l. Hw (Xl) Seq. 1

G C T A G A G G C C A A T T G G A T A T C T A T G A                                                 Consensus #1 -3
                    310                 320
    350   G C T A G A G G C C A A T T G G A T A T C T A T G A                                                 X. l. Hm (Taylor) -4
    301   G C T A G A G G C C A A T T G G A T A T C T A T G A                                                 X. l. Hb (Meighen) -5
    252   G C T A G A G G C C A A T G T G G A T A T C T A T G A                                                 X. l. Hw (Meighen) -6
    252   G C T A G A G G C C A A T C T G G A T A T C T A T T G A                                                 X. l. Hw (Xl) -7
```

Consensus 'Consensus #1': When 50% (2) match the residue of X. l. Hm (Taylor), otherwise show '.'.

Decoration 'Decoration #1': Box residues that match X. l. Hm (Taylor) exactly.

Decoration 'Decoration #2': Shade (with white at 10% fill) residues that differ from X. l. Hm (Taylor).

5,612,184

DEVICE FOR DETECTING MERCURY IN WATER

CROSS REFERENCE TO RELATED APPLICATIONS

This application is a division of Ser. No. 08/111,316 filed Aug. 23, 1993 which is a continuation-in-part of Ser. No. 07/737,951, filed Jul. 30, 1991, now abandoned.

FIELD OF THE INVENTION

This invention pertains devices for the detection of small quantities either of divalent inorganic mercury ion ($Hg^{2+}$) or of both $Hg^{2+}$ and monomethyl mercury in water. These devices comprises bioluminescence detecting means and a bioluminescent biosensory microorganism cells that emit significant light only when exposed to either to $Hg^{2+}$ or to $Hg^{2+}$ or momomethyl mercury.

BACKGROUND OF THE INVENTION

To detect small quantities of mercury in water, atomic absorption spectrophotometry, ion chromatography, gas chromatography or mass spectrometry are typically used. These techniques require expensive equipment and high expertise, and cannot be done quickly, e.g. in minutes. A need exists for a rapid test for mercury that can be used by untrained personnel in the field, at industrial sites, or on the bench in analytical laboratories.

The Microtox® bacterial biosensor (Microbics Corporation) is used for detecting contaminants of an aqueous environment. Luminescence is inhibited by metal ions ($Hg^{2+}$, $Cu^{2+}$, $Cr^{2+}$, $Cd^{2+}$, etc) and organic compounds (sodium lauryl sulfate, formaldehyde, phenol, chloroform, etc) that decreases the metabolic processes of cells. This system is not contaminant specific. It merely indicates the presence of a material that adversely affect metabolism.

S. Frackman et al., *J. Bacteriol.*, 172, 5767–5773, 1990, describe techniques for introducing genomic DNA fragments containing lux genes of *Xenorhabdus luminescens* into plasmids that are introduced into *Escherichia coli* by transformation. Insertion of lux operon fragments and of the complete lux operon into plasmid, the transformation of *Escherichia coli* by plasmid and aldehyde independent and dependent expression of the various lux gene fragments in *E. coli* are reported.

German Patent 3,902,902 discloses that suitably equipped organisms react specifically to the presence of $Hg^{2+}$ by an increase in bioluminescence. A plasmid vector was prepared that contains "narrow spectrum" mercury sensing genes (parts of the mer operon originally from the *E. coli* mercury resistance plasmid R100) that can be induced by $Hg^{2+}$ linked to genes for bacterial luciferase (luxAB) from *Vibrio harveyi* so that $Hg^{2+}$ stimulates expression of the luxAB genes. Upon addition of a long-chain aldehyde, the microorganisms produce light. Microorganisms containing such plasmids can be used to specifically detect $Hg^{2+}$ in water. This test requires the addition of aldehyde to produce bioluminescence.

BRIEF DESCRIPTION OF DRAWINGS

FIG. 15 Nucleotide sequence of pBKS-200 (the Sma I/Xba I 5'-lux fragment of pCGLS200 subcloned into the sequencing vector, pBluescript KS⁻).

FIG. 16 Nucleotide sequence of pBSK⁺205 (the Sma I/Xba I 5'-lux fragment of pJT205 subcloned into the sequencing vector, pBluescript SK⁺). The luxC translation start codon, ATG, is highlighted.

FIG. 17(a)-(b) 5'-luxC sequence of *X. luminescens* Hm (pBSK205⁺; labeled Taylor) aligned against related *X. luminescens* sequences from *X. luminescens* Hb (labeled Meighen) and Hw (labeled Xi and labeled Meighen).

SUMMARY OF THE INVENTION

Figure 1A:
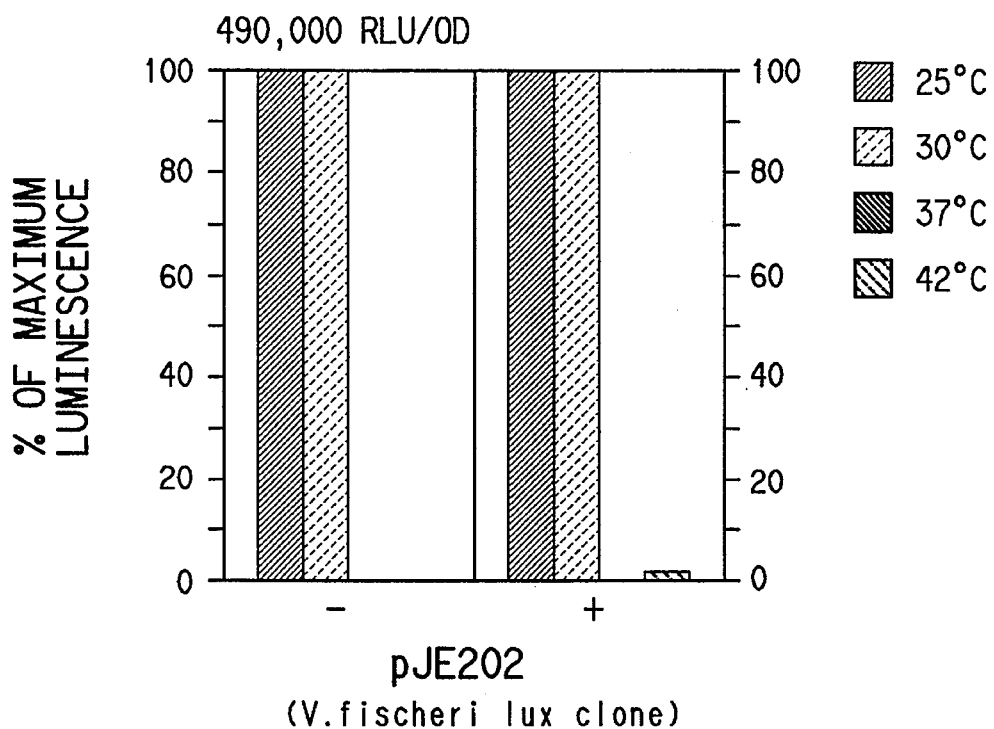
FIG. 1 (*a*)–(*d*) Bioluminescence of Cloned Bacterial lux Operons Over a Range of Temperatures. Cloned lux operons from the terrestrial *Xenorhabdus luminescens* and marine *Vibrio fischeri*, *V. harveyi* and *Photobacterium leiognathi* were incubated at 25 C., 30 C., 37 C. or 42 C. and the luminescence determined.
Figure 1B:
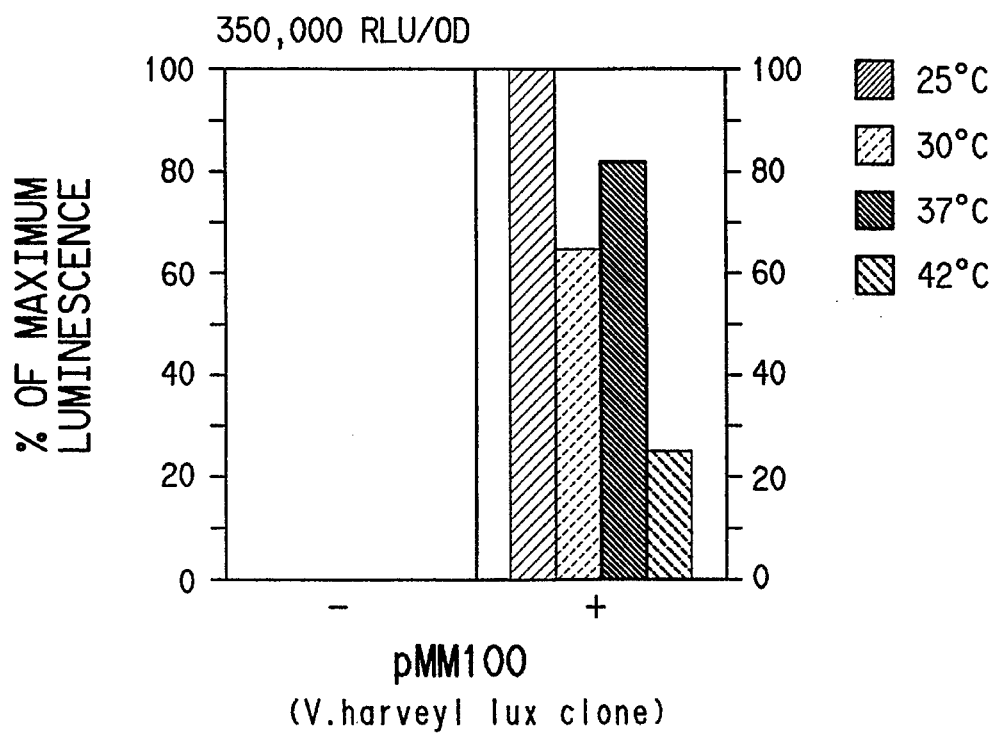
Figure 1C:
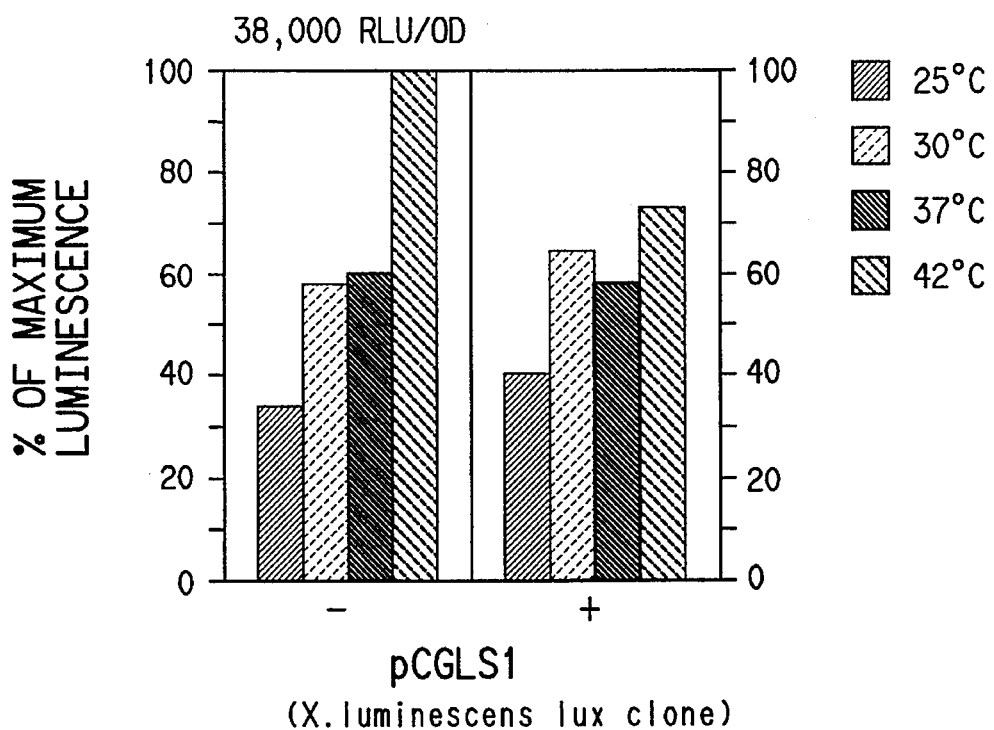
Figure 1D:
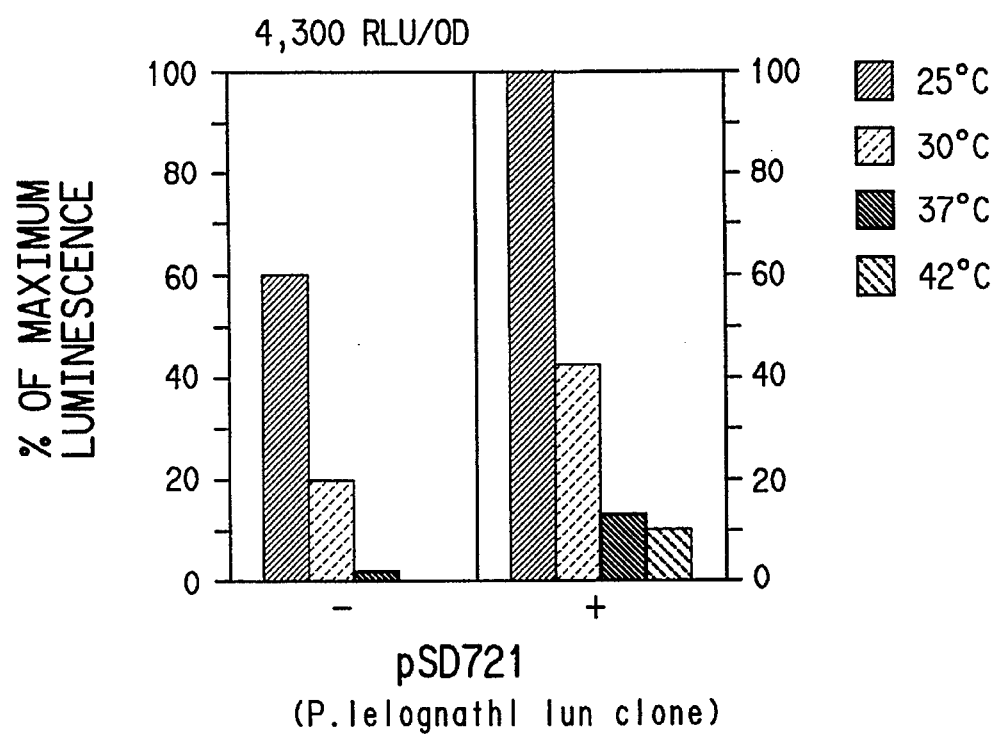

The invention is a plasmid cassette comprising a lux gene operon complex from *Xenorhabdus luminescens*. The lux operon complex comprises luxC, luxD, luxA, luxB, and luxE genes but is free of (1) a promoter for the complex and (2) an inducible regulatory gene for the complex.

In another aspect, the invention is a device for the detection of either (1) divalent mercury ions ($Hg^{2+}$) or (2) divalent mercury ions ($Hg^{2+}$) and/or monomethyl mercury in water, the device comprising:

DETAILED DESCRIPTION OF THE INVENTION

The invention is the promoterless, inducible regulatory gene free lux gene operon complex from *Xenorhabdus luminescens*. Specifically engineered recombinant plasmid cloning vehicles containing this gene cassette have been developed and transformed into competent single host cell carrier microorganisms to produce carrier microorganisms with mercury-specific biosensing capability. A biosensor for detection of small quantities of $Hg^{2+}$ in water has been developed using these cells. This biosensor produces high levels of bioluminescence, operates at temperatures up to 42 C., and does not require the addition of aldehyde.

A biosensor that is sensitive both to $Hg^{2+}$ and to monomethyl mercury has also been developed. This was accomplished by use of plasmids that contain the merB gene. This gene produces the enzyme organomercury lyase., which cleaves monoalkyl mercury compounds, particularly monomethyl mercury, to $Hg^{2+}$. It should be understood that these biosensors are also included in this description.

Recombinant plasmids were prepared by cloning (1) the promoterless bacterial lux operon, (2) a regulatory gene, and (3) an inducible promoter that is activated either by (a) $Hg^{2+}$ or (b) by $Hg^{2+}$ and/or momomethyl mercury into a plasmid cloning vector. An inducible regulatory element was cloned into the multicloning site of the plasmids, immediately upstream of the inserted lux operon. The regulatory element was oriented such that the lux operon was under the control of the newly cloned regulatory element.

The resulting recombinant plasmids were transformed into the cytoplasm of a host microorganism to form biosensor cells. On exposure to $Hg^{2+}$, the regulatory gene initiates expression of the lux operon producing bioluminescence. The amount of light produced is a measure of the concentration of $Hg^{2+}$.

The methods, techniques, and procedures are substantially those found in well known molecular cloning and genetics guides such as: T. Maniatis, et al., *Molecular Cloning; a Laboratory Manual,* Cold Spring Harbor, N.Y., 1982; and Promega *Protocols and Applications Guide,* 2nd edition, Madison, Wis., 1991. Enzymes, plasmids, and other materials are typically available from commercial sources such as: GIBCO/BRL, Gaithersburg, Md. or Promega, Madison, Wis.

PLASMID

The plasmid, or cloning vehicle, into which the regulatory element and the lux operon are cloned contains neither (1) an inducible regulatory element specific to $Hg^{2+}$ or monomethyl mercury nor (2) a lux operon. It should have a multiple cloning site (MCS), or be modified to contain a MCS, receptive to cloning of these genes. A multiple cloning site is a small coding region of the plasmid that contains DNA sequences recognized by several specific restriction enzymes. These specific restriction enzymes cut the plasmid only once and cut only within this region, thereby making it possible to insert foreign DNA into a variety of different sites within the MCS.

The cloning vehicles are, in some cases, multicopy plasmids that individually generate a multiplicity of plasmids. Multicopy plasmids, such as pUC18 and pU19, can be obtained from commercial sources such as GIBCO/BRL, Gaithersburg, Md. A variety of other plasmid cloning vehicles, including low and moderate copy number plasmids, and including narrow and broad host range plasmids, can be used for generating the recombinant plasmid. Examples are listed in Table 1.

TABLE I

Commercially Available Plasmid Cloning Vehicles

| Plasmid | Bacterial System |
| --- | --- |
| pUC18/19 | *Escherichia coli* |
| pBR322 | *Escherichia coli* |
| pMK2004 | *Escherichia coli* |
| pACYC184 | *Escherichia coli* |
| pLG339 | *Escherichia coli* |
| pRK353 | *Escherichia coli* |
| pRK2501 | *Escherichia coli* |
| pUB110 | *Bacillus subtilis* |
| pGC2 | *Bacillus subtilis* |
| pPL531 | *Bacillus subtilis* |
| pPL608 | *Bacillus subtilis* |
| pC194 | *Bacillus subtilis* |
| pK7210 | *Pseudomonas aeruginosa/putida* |
| pKY248 | *Pseudomonas aeruginosa/putida* |
| pKT230 | *Pseudomonas aeruginosa/putida* |
| pFG6 | *Pseudomonas aeruginosa/putida* |
| pGU1106 | *Pseudomonas aeruginosa/putida* |
| pRO1600 | *Pseudomonas aeruginosa/putida* |
| pLAFR33 | *Pseudomonas aeruginosa/putida* |
| pHV14 | *Escherichia coli/Bacillus subtilis* |
| pTE22R | *Escherichia coli/Bacillus subtilis* |
| pBS19 | *Escherichia coli/Bacillus subtilis* |

Recombinant plasmids derived from pUC cloning vehicles also have genes for the α-peptide of the lacZ gene (the MCS is contained within the lacZ gene), and the specific promoter for these genes (Plac). Although this feature is not essential, if it is present in the cloning vehicle, the regulatory elements and the lux genes must be inserted in an orientation opposite to that of the Plac promoter (FIG. 1(a)-(d)), in order to avoid possible non-specific expression of the lux operon by Plac.

The plasmid preferably also contains an antibiotic resistance gene, such as an ampicillin or tetracycline resistance gene. This facilitates selection of the transformed host cells from the general population of host cells. Only transformed cells contain plasmid and are resistant to the antibiotic. The product from cloning and transformation is plated on a solid agar medium containing the given antibiotic for which the transformed cells carry resistance (e.g. 50 μg/mL ampicillin). Transformed cells will form colonies that are dimly luminescent.

HOST CARRIER MICROORGANISM

The host carrier microorganism can be any single cell organism that: (1) is, or can be, made competent for transformation by the recombinant plasmid; (2) does not contain any mechanism that would compete or interfere with the fused regulatory element/lux operons mercury detection mechanism; (3) is not be significantly disabled or killed by contaminants in the media to be tested; (4) does not contain promoters that continuously activate the lux operon to a significant light-emitting degree; and (5) does not contain promoters that induce the lux operon to express significant luminescence in the presence of a contaminant other than mercury.

The host carrier cell can be a bacterium (e.g., *Escherichia coli*, Pseudomonas sp., Bacillus sp.), algae, fungi, yeast or mold, or any of a variety of other single cell organisms that satisfy the above criteria. In most cases, selection of the host carrier is directed by compatibility of transcription of the regulatory element and other genes of interest. This is generally based on the particular standard cloning vehicle from which the lux cassette plasmid was generated, and the general compatibility of a particular DNA with a particular host. Examples of suitable Pseudomonas and Bacillus strains are given Table 2.

TABLE 2

Pseudomonas and Bacillus Strains Suitable as Host Carriers

| Genus/species | Strain |
|---|---|
| Bacillus subtilis | JH642 |
| Bacillus subtilis | TKJ5211 |
| Bacillus subtilis | PS607 |
| Bacillus subtilis | MO0428 |
| Bacillus subtilis | W168 |
| Pseudomonas putida | KT2442 |
| Pseudomonas aeruginosa | PA01 |

In the preferred construction, the host cell is a bacterium. *E. coli* is the most preferred host carrier because it is the best characterized and most easily manipulated system in terms of its genetics and the range of molecular techniques that have been developed for this host carrier. A listing of some of the suitable *E. coli* strains is given in Table 3.

TABLE 3

*Escherichia coli* Strains Suitable as Host Carriers

LE392
C600
DH11
DH5α
DH5αF'Iq
HB101
JM103
JM109
JM83
MC1061
MN294
N99
RR1
TB1
Y1088

Substantially all of the host organisms that are effective carriers of the recombinant DNA plasmids require treatment to render them capable of transformation. This treatment modifies the host cell organisms so they are "competent" to take up exogenous DNA across their cell walls and into their cytoplasm. Bacterial cells are made competent either (1) by chemical treatment of mid-exponential growth phase cells, commonly with high concentrations of $CaCl_2$ or $RbCl$, or (2) by washing and resuspending the cells in low ionic strength buffers to produce electrotransformable cells.

The transformation of host carrier cells can be carried out using known techniques. Competent or electrotransformable cells are mixed with recombinant plasmid DNA. The chemically treated cell/DNA mixture is heat shocked briefly. The electrotransformable cell/DNA mixture is treated with high voltage electrical pulses (electropotation). Treated cell suspensions are allowed to recover briefly and then diluted and plated on suitable growth media such as Luria Broth (LB) agar plates containing an antibiotic such as ampicillin (e.g., for pUC18). If algae, fungi, or molds are to be transformed, the Biolistic Particle Delivery System (E. I. du Pont de Nemours & Co., Wilmington, Del.) may be used to facilitate introduction of lux cassette plasmid DNA into cells.

LUX OPERON

The bacterial lux operon codes for the five structural genes required for luminescence. luxA and luxB encode subunits of bacterial luciferase. luxC, luxD, and luxE encode a fatty acid reductase complex. The enzyme bacterial luciferase requires both oxygen and a long chain aldehyde, provided by the host cell, to produce light.

The lux operon can be obtained from a limited number of marine bacteria. However, the lux operon from the terrestrial *Xenorhabdus luminescens*, a bacterium carried by the nematode *Heterorhabditis bacteriophorce*, has a number of significant advantages. The *X. luminescens* lux operon gives off high intensity luminescence. *X. luminescens* luciferase performs well at elevated temperatures, up to 42 C. In contrast, luciferase from the marine bacteria *Vibrio harveyi* and *V. fischeri* rapidly become inactive at temperatures above 25 C. (see for example, R. Szittner and E. Meighen, *J. Biol. Chem.* 25, 16581–16587, 1990). The *X. luminescens* aldehyde recycling enzyme complex, which is necessary for expression of luminescence, is also stable over a broad range of temperatures (see FIG. 1(a)–(d)). The cloned gene system is complete. When a plasmid containing this operon is transformed into a suitable host cell, all coding elements necessary to produce light are encoded by either the lux operon DNA or are provided by the host cell. There is no need for addition of the aldehyde substrate typically required, for example, when *V. harveyi* lux genes are cloned, or when only the genes for luciferase, luxA and luxB, from *V. harveyi* or *V. fischeri* are cloned. This is a substantial improvement over systems that require addition of exogenous aldehyde to produce a bioluminescent response.

Figure 2:
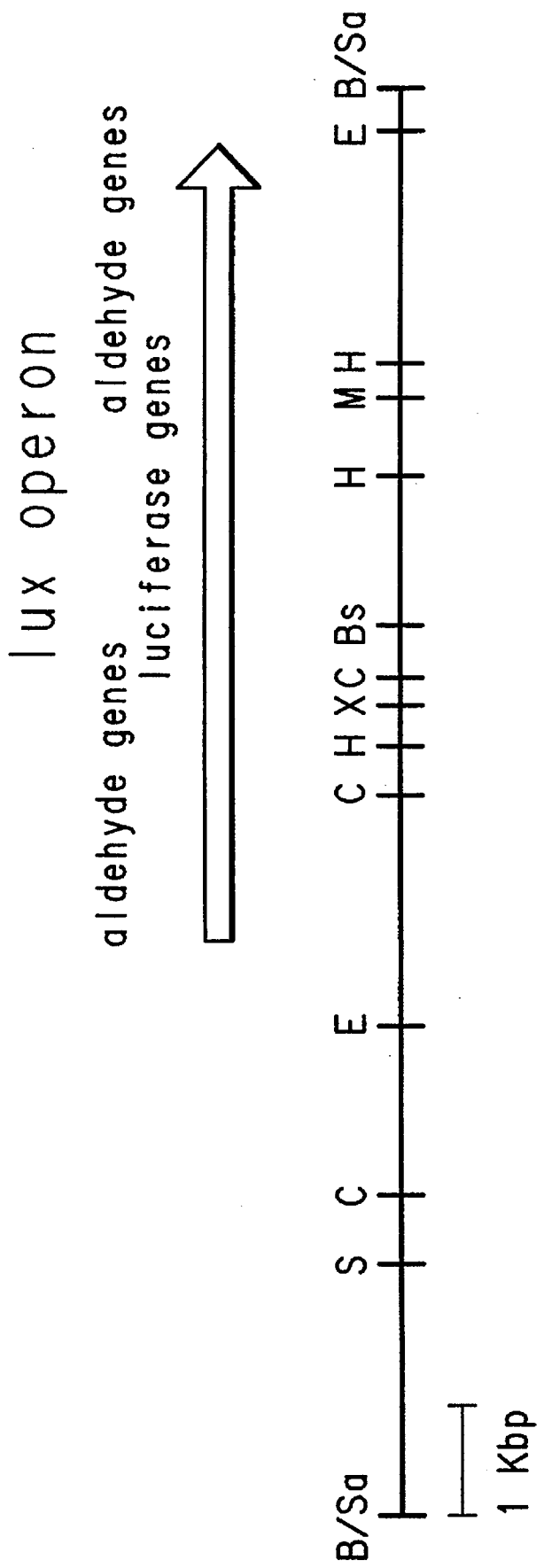
FIG. 2 Partial restriction map of lux operon from *Xenorhabdus luminescens* and the direction of transcription (arrow). Restriction endonuclease sites are abbreviated as follows: Bs, BstE II; C, Cla I; E, EcoR I; H, Hind III, M, Mlu I; S, Sca I; X, Xba I; B/Sa represents the joining of BamH I and Sau3a-cut DNA.

The lux operon from *X. luminescens* has been cloned into pUG18, and the cloned operon has been partially characterized by Frackman. The lux operon DNA is found on an 11 Kb insert in plasmid pCGLSl (see FIG. 2). Frackman discloses that EcoR I restriction enzyme digestion of pCGLSl generates a fragment of about 6.9 Kb (pCGLS11 and 11 r). Frackman speculated that this fragment appeared to lack its natural promoter region. Frackman showed when this fragment is religated into pUC18 and transformed into a suitable *E. coli* host, the transformed cells produce light in either orientation relative to the lac promoter; seven fold higher light was measured when the fragment was under lac promoter control. Frackman did not report relative light levels produced by pCGLS11, only ratios of light emission.

For an operational biosensor based on a lux reporter system, it is desirable to minimize background light and to maximize the signal to noise ratio of the biosensor. This can be accomplished by complete removal of both the natural regulator and the natural promoter region. Therefore, a pCGLS11-like construct, designated pCGLS200, similar to that reported by Frackman, was created from pCGLS1. This plasmid, when transformed into *E. coli,* produced moderate levels of light.

It is has been possible to eliminate the natural lux operon promoter from *X. luminescens.* Microorganisms in which there is minimal expression of the lux operon have been developed, so that background luminescence is very low. The removal of the natural regulator promoter of the *X. luminescens* lux operon was achieved, for the first time, in this invention and verified by nucleotide sequencing. Representative lux cassette plasmids of the invention are shown in Table 4.

TABLE 4

Recombinant lux cassette plasmids derived from *X. luminescens lux* operon.

| lux cassette plasmid | Comments |
| --- | --- |
| pCGLS200 | A 6.9 kb EcoR I fragment from pCGLS1 containing lux structural genes in the plasmid pUC18; moderate background luminescence. |
| pJT204 (pCGLS204) | An ~6.4 kb fragment resulting from Bal31 digestion of pCGLS200 lux insert; dim (20X lower than PCGLS200) background luminescence. |
| pJT205 (pCGLS205) | An ~6.4 kb fragment resulting from Bal31 digestion of pCGLS200 lux insert; very dim (35X lower than pCGLS200) background luminescence. |
| pRPB78 | A promoterless tet antibiotic resistance gene fused to lux in pJT205; very dim (35X lower than pCGLS200) background luminescence. |

REGULATORY GENE LUX CASSETTE CLONING VECTOR

This invention incorporates the engineering of new recombinant plasmids from known cloning vehicles that contain promoterless lux operons. These new recombinant plasmids are known as "regulatory gene lux cassette cloning vectors" or simply "lux cassette plasmid." Such new recombinant plasmids are used to isolate and clone the inducible regulatory elements of interest. Upon introduction by ligation of the regulatory element of interest into the lux cassette plasmid, followed by transformation of this recombinant plasmid into a suitable host carrier, a unique biosensor for a particular material is formed.

REGULATORY ELEMENTS

The inducible regulatory gene(s) is taken from plasmids or from genomic DNA in bacterial strains that are resistant to attack by $Hg^{2+}$ ions or by both $Hg^{2+}$ ions and monomethyl mercury. Some Serratia sp., for example, are known to be resistant both $Hg^{2+}$ ions and to monomethyl mercury. In its parent bacterium the gene(s) and its promoter/operator function to initiate protective activity upon exposure to $Hg^{2+}$ ions or to momomethyl mercury.

Plasmids containing inducible regulatory gene(s) and resistance gene(s) can be maintained and propagated in appropriate host cells using standard techniques. These plasmids can also be extracted from the host bacteria, purified, and stored in a frozen state using known techniques.

MERCURY BIOSENSOR

The mercury biosensor comprises an aqueous suspension of engineered that are bioluminescent in the presence of either (1) $Hg^{2+}$ ions or (2) $Hg^{2+}$ ions and/or monomethyl mercury operably connected to a means for detecting bioluminescence. Operably connected means that the detecting means is/arranged in such a fashion that it can detect bioluminescence from the engineered biosensory microorganism cells. Bioluminescence is conveyed from the biosensory cells to the detection means by a means for conveying bioluminescence. As described below, this can be accomplished, for example by placing a receptacle that is substantially transparent to bioluminescence and which contains the suspension on a photographic film, by placing a photomultiplier adjacent to a receptacle containing the suspension, by conveying the bioluminescence from the receptacle to the detecting means by a fiber optic bundle, etc.

The aqueous suspension is contained in receptacle, i.e, a test tube, a screw top vial, a cuvette, a multiwell plate, or similar container. The receptacle must have a means for conveying bioluminescence from the aqueous suspension to the detecting means. The is typically accomplished by using a receptacle at least a portion of the which is substantially transparent to the bioluminescence. The receptacle may be made of a material that is substantially transparent to bioluminescence, such as, for example, glass, quartz, poly(methyl methacrylate), etc, or it may contain a window made from a substantially transparent material. The receptacle is placed in a light-tight container so that the means for detecting bioluminescence detects only the light emitted by the biosensory cells. The conveying means may additionally comprise a properly shielded fiber optic cable either placed in close proximity to the receptacle, or attached to the receptacle, in such a fashion that it conveys bioluminescence from the suspension to the detecting means.

Alternatively, the means for conveying bioluminescence from the aqueous suspension to the detecting means may comprise a properly shielded fiber optic bundle inserted in the aqueous suspension or attached to a transparent portion the receptacle. In this arrangement the rest of the receptacle can be opaque and combine the functions of both the receptacle and the light-tight container. Such an arrangement is equivalent to a receptacle and a light-tight container.

The means for detecting bioluminescence can be of several types, depending on the method of use. The detecting means can be, for example, the human eye, photographic film, a photomultiplier, a photodiode, etc. The detecting means may additionally comprise a metering device and/or a computer for storing data and calculating the concentration of mercury present in the sample. Desirably, the means for detecting bioluminescence will measure intensity of light as a function of concentration of mercury.

The presence or absence or mercury may sometimes be ascertained by visual observation of the receptacle containing the aqueous suspension and the sample. Preferably observation is made in a darkened area and in conjunction with one or more standards and/or blanks.

A photographic film is a useful detection means for qualitative measurements. This means comprises a photographic film, for example, a Polaroid® instant photographic film (Polaroid Corp), such as Type 667, that is exposed by bioluminescence from biosensor cells. The film is covered with a masking plate and a block with holes placed on top of the masking plate. One or more vials, each containing an aqueous suspension of biosensory cells, are inserted into the holes in the block so that their bases are exposed to the film. The bases of the vials must be substantially transparent to bioluminescence. Multiple samples may be analyzed may simultaneously, typically in conjunction with a one or more standards and one or more blanks. After the vials are placed in the block, a cover is placed over the film, vials and block to prevent light from exposing the film. Measured volumes of samples are injected into the vials, each of which contains a known volume or concentration of biosensor cells. The making plate is removed in such a way that the film is not exposed to ambient light. After exposure of the film to any bioluminescence from the vials, the masking plate between the vials and the film is replaced, the film is developed and the intensity of each spot bioluminescence noted. The presence, clarity and brightness of the spots indicates whether mercury is present in each sample and indicate its concentration.

One portable photomultiplier, such as a Hamamatsu Corporation 1894, may be used as a detecting means. This means comprises a head-on tube and a light-tight chamber (sample holder). The photomultiplier provides a strong response in the 500 nm range of bioluminescent output. The amplifier and high voltage power supply are battery powered for portability. The receptacle and photomultiplier are so situated that the photomultiplier can detect the bioluminescence from the biosensory cells in the receptacles. The receptacles are loaded into the sample holder and bioluminescence measured by the photomultiplier. Such sample holder/photomultiplier arrangements are well known to those skilled in the art. A data acquisition/computer system can be used to automate the sample logging process.

Another photomultiplier primarily for laboratory use is the side-on tube photomultiplier type, such as a Hamamatsu R363 side-on tube. This photomultiplier exhibits exceptionally flat response across the range of the light output of the biosensor cells. The system has a light-tight chamber (sample holder) for discrete testing of samples and a digital panel output meter. The photomultiplier amplifier is designed around an Analog Devices electrometer operational amplifier (an AD515). The electrometer amplifier is operated as a current-to-voltage converter using a switched series of high-value resistors (100 Kohm to 100 Mohm). In addition, noise damping is included by wiring manually switched low-value capacitors in parallel with the gain resistors. The output of the amplifier is calibrated with a calibrated, industry-standard amplifier (Pacific Photometrics Model 110 Photometer) using the same photomultiplier tube with a 4.5 digit readout voltmeter. Agreement between the two amplifiers is within the precision and repeatability of the light source. A data acquisition/computer system can be used to automate the sample logging process.

The photodiode photometer is designed primarily for field use. The instrument is built using an instrumentation amplifier and a Hamamatsu photodiode subunit. This Hamamatsu HC220-01 has an integral fixed-gain amplifier with optional external offset adjustment. The sensitivity is 0.8 V/nW at the peak wavelength sensitivity at 720 nm. The instrumentation amplifier provides additional gain which is adjustable from a factor of 15 to 30,000, and greatly reduces noise at high gain. The readout is a digital voltmeter (DVM). This photodiode photometer readily detects the output of a laboratory standard light source constructed from $^{14}CO_2$ in scintillation flour and sealed in a glass ampoule, a precision of +2% is obtained and is limited primarily by geometric effects as the standard light source is much smaller than the sample vial.

The sensitivity and linearity of these photometers is determined by comparing the response of the photodiode instrument with the laboratory-standard photomultiplier photometer using bioluminescent cultures. The photodiode photometer is fully capable of accurately quantifying bioluminescence of bacterial cultures. When fully derepressed bacteria are used, the output of the solid-state photometer becomes nonlinear, indicating that the sensor is saturated.

To prepare the detection device, the biosensory microorganism cells are put into growth medium such as Luria Broth (LB) or a M9 Mineral Salts plus Glycerol plus Cysteine medium (M9 medium) at a predetermined microorganism concentration, and the aqueous microorganism suspension is then associated with means for exposing the microorganism to the media to be tested and the means for detecting a bioluminescence signal.

In use, the aqueous medium to be tested for mercury, i.e., the sample, is introduced into the aqueous suspension of microorganisms. The sample may be simply introduced by pouring it into the receptacle or adding it to the receptacle from a volumetric pipette. Or, if the receptacle is covered with a serum cap, it can be injected through the serum cap using a syringe. Mixing is typically accomplished by agitating the sample, i.e., by stirring, shaking, swirling, etc. If the sample contains divalent mercury ions or monomethyl mercury, the regulatory elements will stimulate transcription and translation of the lux operon, causing bioluminescence. The bioluminescence is sensed by the means for detecting bioluminescence. The intensity of the bioluminescence can be used to indicate the concentration of material present.

The inducible regulatory gene that is cloned into the plasmid base of the lux cassette plasmid is sensitive to either (1) to $Hg^{2+}$ ions or (2) to both $Hg^{2+}$ ions and monomethyl mercury. When exposed to these materials, the regulatory element signals expression from the lux operon that has also been cloned into the plasmid. Representative mercury biosensors responsive to $Hg^{2+}$, or to both $Hg^{2+}$ and monomethyl mercury, are shown in Table 5. Two of these biosensors (pKL152 and pKL48) also incorporate specific resistance to mercury.

TABLE 5

Recombinant mer plasmids derived from mer fragments of mGN2-220 or pGN110 and lux cassette plasmid.

| Recombinant mer::lux plasmid | Source lux cassette plasmid | Comments |
| --- | --- | --- |
| pCGLS201 | pCGLS200 | $merR_{O/P}TAP::lux$; $Hg^{2+}$ biosensor |
| pJT206 (pCGLS206) | pJT204 | $merR_{O/P}TAP::lux$; $Hg^{2+}$ biosensor |
| pJT207 (pCGLS207) | pJT205 | $merR_{O/P}TAP::lux$; $Hg^{2+}$ biosensor |
| pKL156 | pRPB78 | $merR_{O/P}\Delta T::lux$; $Hg^{2+}$ biosensor |
| pKL152 | pJT205 | $merR_{O/P}TPA::lux$; $Hg^{2+}$ resistance and biosensor |
| pKL48 | pJT205 | $merR_{O/P}TPAB::lux$; $Hg^{2+}$ and monomethyl mercury resistance and biosensor |

INDUSTRIAL APPLICABILITY

This invention is a device for detection of small quantities of $Hg^{2+}$ and monomethyl mercury in aqueous media. The biosensor is sensitive, selective, specific, nondestructive, and easy-to-use. It is capable of qualitatively and quantitatively detecting divalent mercury in the parts per billion (ppb) to million (ppm) range and of methyl mercury in the ppm range. The test is rapid, requiring only 15 to 30 minutes at 30 C.; the test can be run between 25 C. (ambient temperature) and 42 C. The biosensor can be used by untrained personnel in the field, at industrial sites, or on the bench in analytical and clinical laboratories and is adaptable to spot tests, automated on-line continuous monitoring, and on-line process control.

The biosensor can be used for water-quality testing at consumer and industrial levels. Consumer tests include drinking water, both municipal and well water, and recreational waters. Industrial tests include municipal water works, well water, water, industrial supply and effluent waters, sewage treatment plant inflow and treated wastewater, and environmental analysis of groundwater and soil. Canned goods, frozen foods, and perishable products can also be tested. The test can also be applied to medical diagnostics such as measurements of $Hg^{2+}$ and monomethyl mercury in blood, urine or tissue specimens.

EXAMPLE 1

This example illustrates the differing temperature stability and aldehyde dependence of the luminescence from cloned terrestrial and marine lux operons.

*E. coli* cells carrying plasmids with inserted lux operons from *Vibrio fischeri* (pJE202; in pBR322), *Vibrio harveyi* (pMM100; in pBR322), *Xenorhabdus luminescens* (pCGLS1; in pUC18), or *Photobacterium leiognathi* (pSD721; in pACYC184) were prepared by the transformation procedure of Example 4. The cells were grown with vigorous agitation in Luria Broth at various temperatures between 25 C. and 42 C. to an optical density (600 nm) of about 1.0. Luminescence was measured with a photomultiplier-based luminometer in the presence and absence of decylaldehyde. Results are shown in FIG. 1.

The most temperature stable lux operon was that of *X. luminescens* (pCGLS1). Increasing light levels were produced at temperatures as high as 42 C. The luminescent response was independent of aldehyde at all temperatures tested. The expression of luminescence by cloned lux operons of *V. fischeri*, *Vibrio harveyi*, and *Photobacterium leiognathi* was strongly inhibited at temperatures greater than 30 C.

EXAMPLE 2

This example illustrates generation of a plasmid cassette comprising the lux operon complex (luxCDABE) from *X. luminescens*. The cassette contains neither a natural inducible regulatory gene nor a natural promoter for the complex.

The EcoR I fragment of the pCGLS1 lux operon (see FIG. 2), containing lux structural genes, was cloned into one end of the MCS of the cloning vector, pUC18 by known techniques. Specifically, 1 μg of preferably CsCl-purified pCGLS1 DNA was digested with the site-specific restriction enzyme, EcoR I. The digested pCGLS1 DNA was separated onto component fragments by horizontal electrophoresis in an agarose gel (0.8–1.0% w/v agarose) in 0.5–1 X TBE buffer. A DNA fragment corresponding to the size of 6.9 kb was identified and excised from the gel and eluted by known techniques such as extraction with glass milk (GeneClean II®, Bio101, Inc., La Jolla, Calif.) or a freeze-squeeze method; pUC18 was similarly digested with EcoR I to linearize the circular plasmid and to prepare the plasmid for incorporation of the lux operon fragment. The eluted fragment was mixed with the linearized pUG18 plasmid, and upon addition of T4 DNA ligase, buffer, and after appropriate incubation conditions (Maniatis et al.), the EcoR I DNA fragment containing the structural lux genes was incorporated (ligated) into the plasmid (see FIG. 3). This new recombinant plasmid was designated pCGLS200 (Table 4).

This cloned lux operon was selected to contain all necessary structural genes (luxC, luxD, luxA, luxB and luxE) to support expression of bioluminescence. This operon was cloned into the EcoR I MCS of pUG18 at the 3' end of the MCS proximal to Plac. It was essential that the operon be oriented such that the 5'-transcriptional orientation of the operon was opposite to the 5'-transcriptional orientation of Plac. In the recombinant plasmid pCGLS200, digestion of the plasmid with Xba I yielded two bands when the products of the digestion were electrophoresed, as previously described, in an agarose gel. A clone with the correct lux orientation generated fragments of about 2.5 kb and 7.2 kb, while the incorrect orientation generated fragments of about 4.5 kb and 5.2 kb. This construct had a moderate background luminescence in the absence of mercury of about 4,000 Relative Light Units (RLU) when grown to late exponential phase to early stationary phase.

Figure 3:
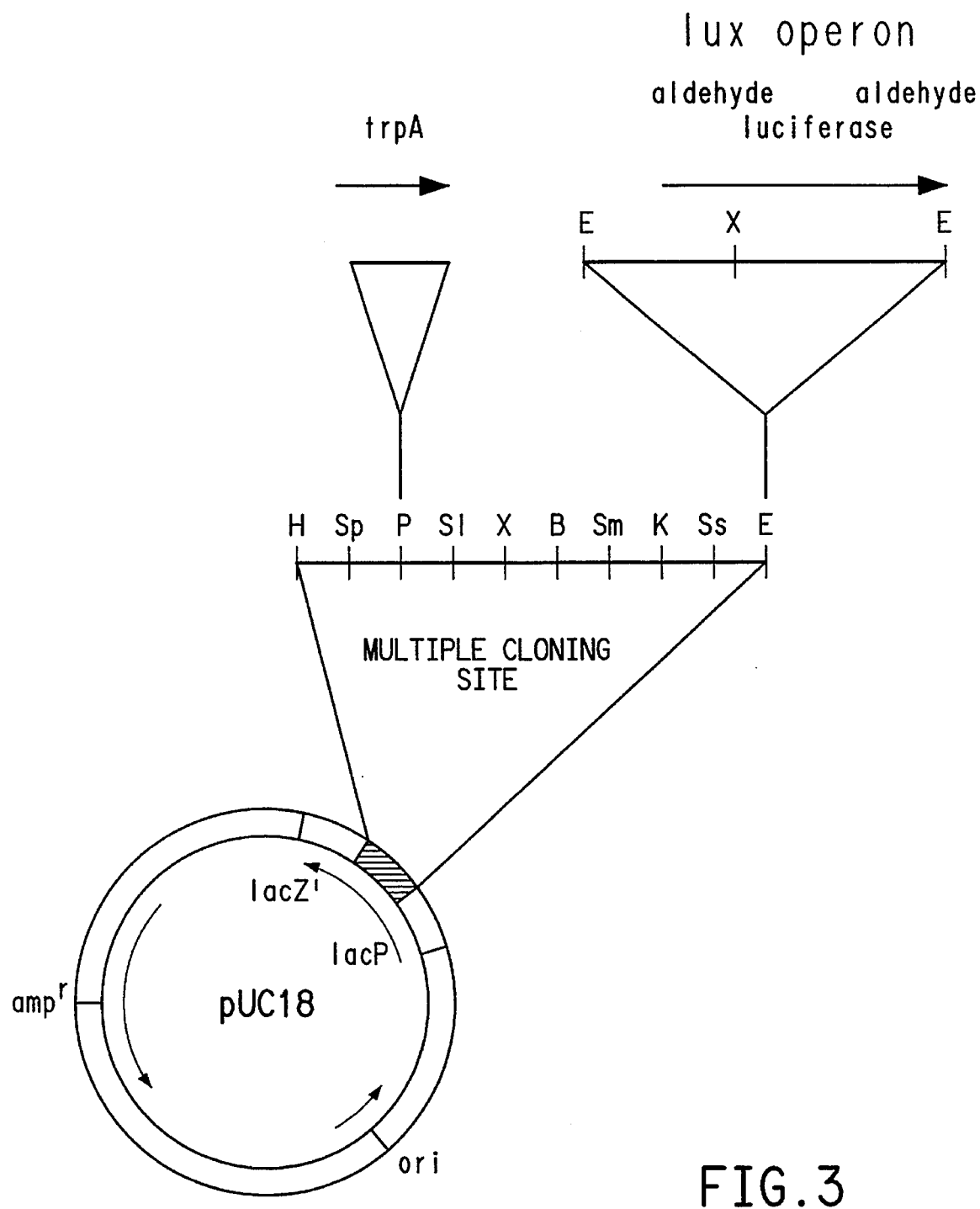
FIG. 3 Schematic representation of lux cassette plasmid (pCGLS200) showing the original pUC18 cloning vector, representative restriction sites, direction of transcription of the various elements (arrows) of the *X. luminescens* lux operon and a transcription terminator. Restriction endonuclease sites are abbreviated as follows: H, Hind III; Sp, Sph I; P, Pst I; SI, Sal I; X, Xba I; B, BamH I; Sm, Sma I; K, Kpn I; Ss, Sst I; E, EcoR I.
Figure 4:
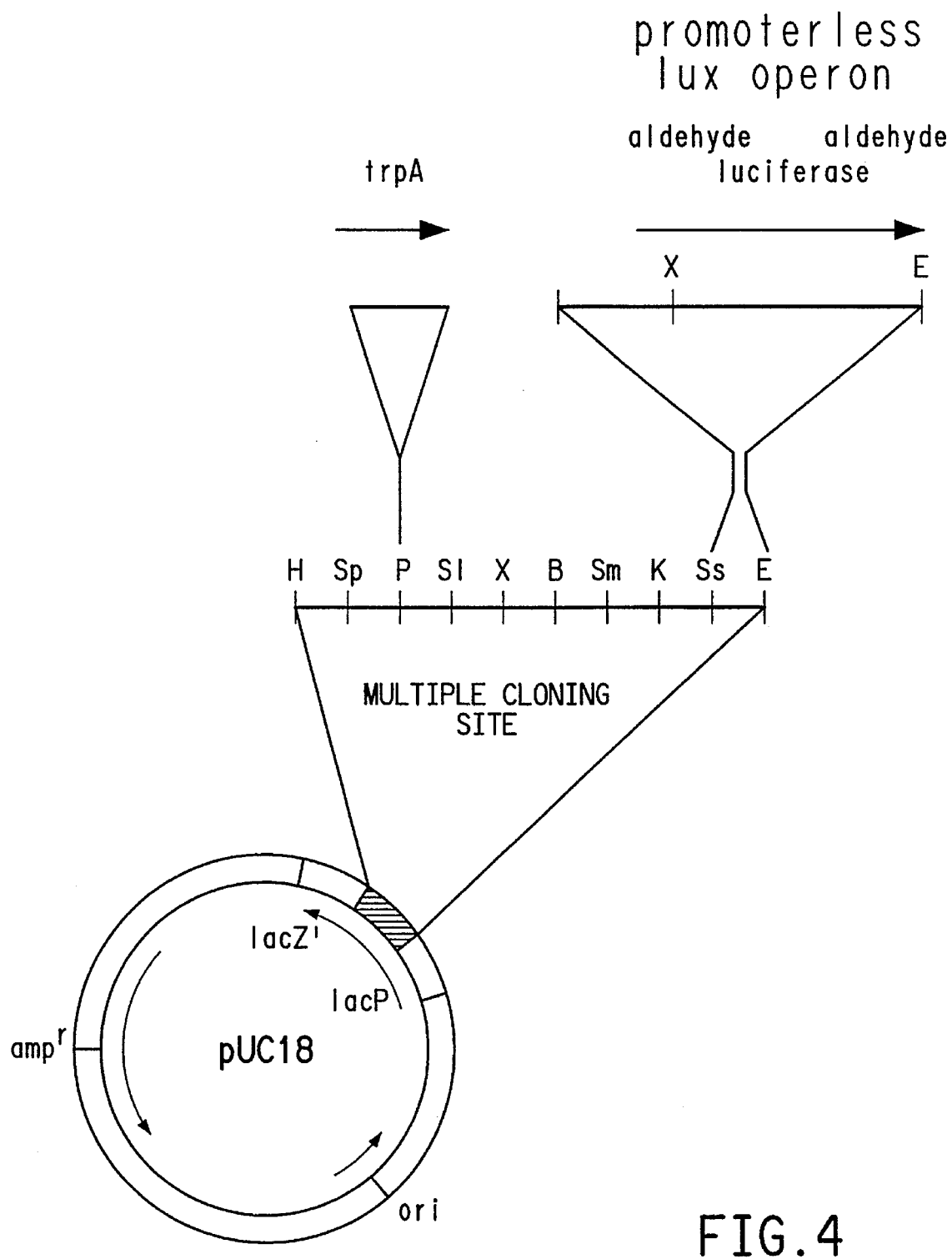
FIG. 4 Schematic representation of the preferred lux cassette plasmid (pJT205) showing the original pUC18 cloning vector, representative restriction sites, direction of transcription of the various elements (arrows) of the promoterless *X. luminescens* lux operon and a transcription terminator.

It was possible to further reduce the background luminescence of the lux cassette plasmid by removing DNA from the upstream, 5'-end of the lux operon. by digesting pCGLS200 with Kpn I. A linearized plasmid, cut within the MCS just upstream of the lux operon, was produced. (FIG. 3).

The linearized plasmid was treated by known techniques with Nuclease Bal31 for 2, 3, 4, 5 and 6 min. Nuclease Bal31 cleaves linear duplex DNA exonucleolytically from both ends, producing successively shortened strands. Cleavage results in mostly blunt ends. Only the 3'-end of the lux operon was protected by plasmid DNA. The loss of this 3'-plasmid DNA was of no consequence, as the cut-down lux operon was ultimately removed from this modified plasmid and only the downsized lux operon was religated into now whole pUC18.

At the times indicated, the digestions were terminated by heating using known techniques. The Nuclease Bal31 digestions were sized on agarose gels and those digestions that yielded deletions of approximately 500 bp were selected for further study. The appropriate digestions were then precipitated with ethanol and resuspended in 10 mM Tris, 1 mM EDTA, pH 8.0 (TE) using known methodology.

Nuclease Bal31 deletions destroyed the Kpn I site at which the plasmid was originally linearized (this site was the first to be deleted). Therefore, molecular linkers with appropriate restriction sites were ligated to the plasmid to facilitate circularization of the plasmid. The appropriate Nuclease Bal31 digestions were prepared for blunt end ligation with phosphorylated molecular linkers by any one of three methods: (1) no further treatment; (2) treatment with Mung Bean Nuclease (an exonuclease that processes single strand ends producing blunt ends); or (3) treatment of the ends with the large fragment of DNA Polymerase I (Klenow fragment) plus deoxyribotrinucleotides to fill in overhangs and thus produce blunt ends.

Phosphorylated Sst I or Kpn I molecular linkers were then ligated with T4 DNA ligase to the untreated and treated Nuclease Bal31 digestions. Modified ligated plasmids were cut with the appropriate restriction enzyme, either Sst I or Kpn I, in order to linearize the circularized plasmid and to eliminate concatamers of linkers possibly formed during linker ligation. Unincorporated linkers were removed by ethanol precipitation or spin column treatment using known techniques.

The clean, linearized plasmids were then circularized by ligation, then transformed into a suitable host, and dim or dark colonies were selected. Two of these were picked and designated pJT202 (from ligation with Sst I linkers) and pJT203 (from ligation with Kpn I linkers) (see Table 4).

Intact lux cassette plasmids were regenerated by removing the modified (by deletion) lux operon inserts from pJT202 by double digestion with EcoR I/Sst I, and from pJT203 by double digestion with EcoR I/Kpn I. The respective lux inserts were purified by electrophoresis on agarose gels, followed by excision and purification of the appropriate bands as described above. Directed ligation into new pUC18 was achieved by doubly digesting new pUC18 plasmid with either EcoR I/Sst I or EcoR I/Kpn I, followed by standard ligation of the purified lux inserts into the appropriate linearized plasmid. The resulting plasmids were designated pJT204 and pJT205 (Table 4). These plasmids have dim (200 RLU) and very dim (100 RLU) background luminescence.

A further enhancement of the lux cassette plasmid was achieved by inserting, downstream of the promoterless lux operon, a promoterless tetracycline (tet) antibiotic resistance gene. In preparation for insertion of an antibiotic resistance cassette, a Xho I site was introduced into the unique EcoR I site of pJT205. pJT205 was digested with EcoR I and the sticky ends filled-in with Klenow and dNTPs. Nonphosphorylated Xho I linkers were ligated to the blunted ends. The Xho I-terminated fragments were purified and concentrated by spermine precipitation. This DNA was then circularized by ligation and the ligation mixture was used to transform *E. coli* DH5α. The transformation preparations were plated on LB-AMP and recombinant colonies were picked. The appropriate clones had a single Xho I site flanked by a pair of EcoR I sites; this was confirmed by restriction digestion analysis. A representative clone, pKPB71, was used for further work.

A tetracycline gene (TET GenBlock, Pharmacia LKB, Milwaukee, Wis.) was selected. pRPB71 was digested with Xho I and blunt-ended with Klenow and dNTPs. The tet cassette was digested with Mse I, which removes the tet promoter from the structural gene by cutting at position 56. This DNA was then filled in with Klenow and dNTPs and agarose gel purified. The large fragment was ligated to linearized, blunt-ended pKPB71. This yielded a plasmid with promoterless tet resistance, bounded by EcoR I sites, immediately downstream of lux (pRPB78; Table 4). An internal BamH I site was used to confirm the appropriate tet orientation relative to the lux. The absence of sites upstream of Mse I was confirmed by restriction mapping.

In some combinations of the above described lux cassette plasmid, and with certain host microorganisms, background luminescence may still be excessive. In such cases, it may be desirable to insert into the lux cassette plasmid a Transcription Terminator such as trpA or rrnB (Pharmacia LKB BioTechnology, Milwaukee, Wis.) upstream of the lux operon and upstream of the intended site of cloning of an inducible regulatory element, for example, the Pst I site in the MCS (FIG. 3). The Transcription Terminator is modified by addition of Pst I phosphorylated linkers by ligation with T4 DNA ligase. The product of the ligation is cut with Pst I using known standard conditions. The ligated product is purified by precipitation with ethanol or by spin column. lux cassette plasmids, such as pJT204 and pJT205 are also cut with Pst I and the Transcription Terminator-linker product is ligated into the plasmid as previously describe. After transformation into suitable competent host carriers, transformed host cells are selected randomly from those that grow on LB-AMP plates. Clones with the Transcription Terminator in the proper orientation to the lux operon will be very dim or dark. The presence and confirmation of the proper orientation of the Transcription Terminator can be achieved by subcloning the MCS containing the Transcription Terminator into an M13 sequencing system using known techniques, and verifying the presence and orientation of the Transcription Terminator by analysis of the nucleotide sequence.

The Transcription Terminator incorporated into the lux cassette plasmid will prevent transcription of the lux operon in the absence of expression from a cloned regulatory gene. By this technique, clones with exceptionally low background luminescence can be prepared.

EXAMPLE 3

This example demonstrates a native, promoterless *X. luminescens* lux operon.

The 5'-regions of plasmids pCGLS200 and pJT205 were sequenced using the dideoxy chain termination method (T. S. Hultman et at., *Nuc. Acids Res.*, 17, 4937–4945, 1989; F. S. Sanger et al., *Proc. Natl. Acad. Sci. USA*, 74, 5463–5467, 1977) using a modified T7 polymerase (Sequenase®, United States Biochemicals, Cleveland, Ohio). The plasmids were linearized by digestion with restriction enzymes that cut the MCS upstream of the lux operon DNA and within the lux operon DNA downstream of luxC. These plasmids were linearized by digestion with Sma I (in the MCS) and Xba I (in luxD). 5'-lux operon fragments of 2.5 kb (pCGLS200) and 2.0 kb (pJT205) were gel purified. Subcloning of these fragments was done in a directed fashion; as one end (5') was blunt and the other (3') was sticky. The sequencing vectors (2.96 kb), pBluescript KS- and pBluescript SK$^+$ (Stratagene, La Jolla, Calif.), were also linearized with Sma I and Xba I. The linearized vectors and the appropriate lux fragments were mixed and ligated. Competent *E. coli* XL1-Blue (Stratagene, La Jolla, Calif.) cell suspensions were transformed with the recombinant pBluescript-lux vectors. Transformed cells were plated onto LB-AMP with tetracycline, IPTG, and Xgal; white colonies were selected. Verification of the insert in selected clones was determined by digestion of miniprep plasmid DNA with Pst I and Xba I.

Single-stranded DNA was prepared according to Stratagene's protocol (Stratagene, La Jolla, Cailf.). Cultures were grown in Superbroth supplemented with ampicillin and tetracycline with VCSM13 helper phage. Cells were removed by centrifugation and the phage in the supernatant were precipitated with polyethylene glycol. Single-stranded DNA was extracted from the pellets with phenol:chloroform.

The Stratagene KS primer (17 mer) was used for sequencing; labeling was with $^{35}$S-dATP. Aliquots of sequence reactions were electrophoresed on 0.4 mm×45 cm 5% Long Ranger® Gels (Hydrolink). The gels were dried and exposed to X-Ray Film (X-OMAT AR, Kodak). The nucleotide sequence was read from the resulting autoradiographs. The sequences for the lux fragments (5' to 3') from the pCGLS200 (pBKS-200) and pJT205 (pBSK$^+$ 205) are shown in FIGS. 15 and 16. No overlap between the 5'-lux sequence of pCGLS200 and pJT205 was detected (compare the sequences in FIG. 15 to those in FIG. 16). This suggests that the Nuclease Bal31 deletion that generated the pJT205 lux cassette was greater than 501 bp.

Figure 17A:
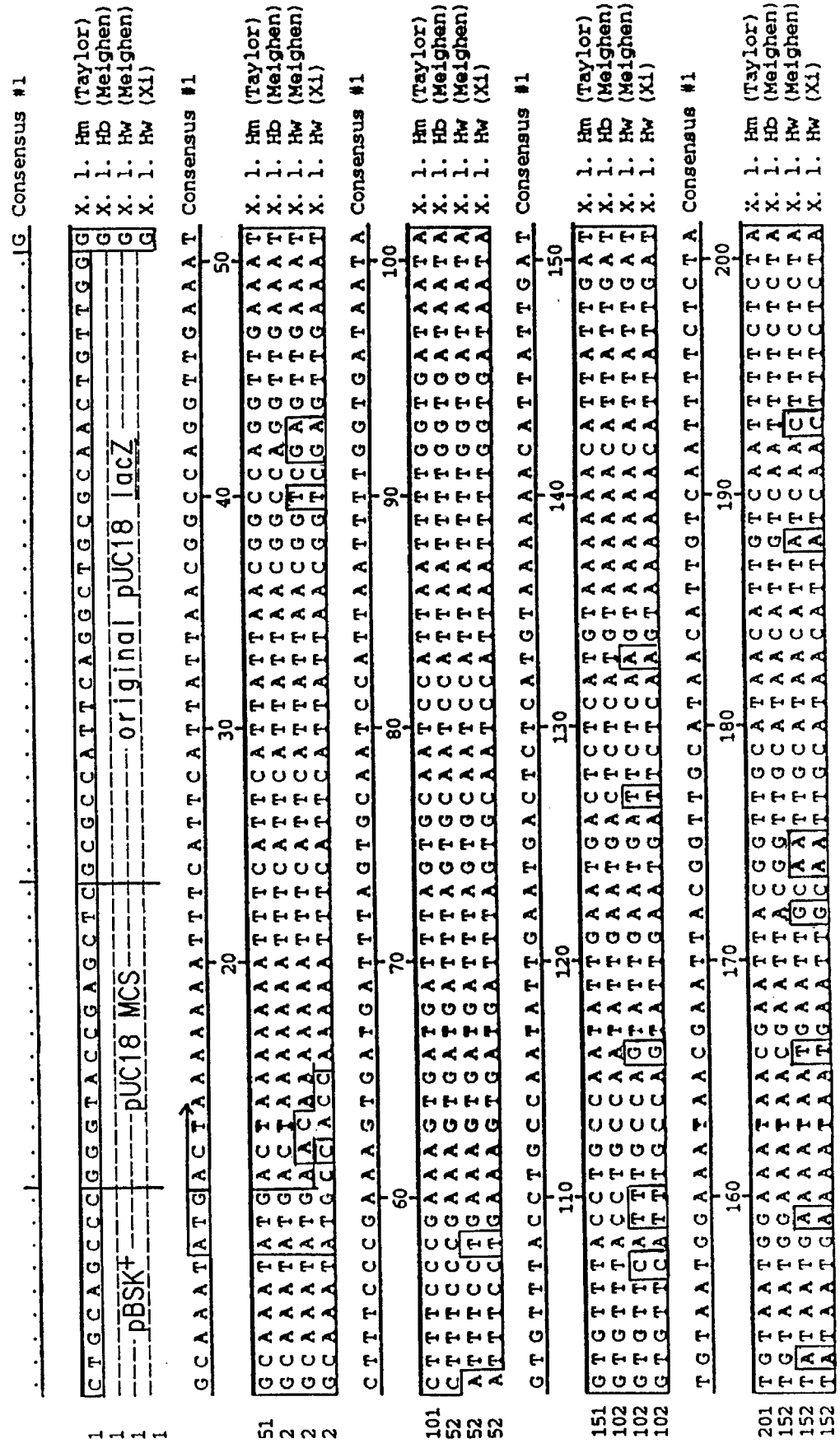

*X. luminescens* Hm luxC sequence has not been previously published. The nucleotide sequence of the related *X. luminescens* Hb lux operon was published by Meighen and Szittner, *J. Biol. Chem.*, 265, 16581–16587, 1990. The luxC sequence (including 30 base pairs immediately upstream) from the related *X. luminescens* Hw (originally isolated from a human wound) was published by Xi et al., *J. Bacteriol.*, 173, 1399–2405, 1991 and by Meighen and Szittner, *J. Bacteriol.*, 174, 5371–5381, 1992. The luxC sequence from *V. harveyi* was published by Miyamoto et al., *Nuc. Acids Res.*, 16, 1551–1562, 1988; there was no identifiable correlation of the *X. luminescens* Hm and *V. harveyi* luxC sequences or with luxC sequence from other Vibrio spp. or Photobacterium spp. A comparison of aligned pBSK$^+$ 205 (5' luxC sequence from *X. luminescens* Hm; lux insert in pJT207), and *X. luminescens* Hb and Hw sequence indicates that all but 8 base pairs of the upstream sequence proximal to luxC were deleted (note pBSK$^+$ 205 sequence, bp #49–56; FIG. 17(a)–(b)). The remainder of the leading sequence of pBSK$^+$ 205 could be accounted for by pBluescript (bp #1–9), pUC18 MCS (bp 10–22), and the distal portion of lacZ from pJT202 (bp #23–48). This sequencing effort confirmed that the natural promoter was deleted from the lux operon.

EXAMPLE 4

This example illustrates a mercury biosensor that responds specifically to $Hg^{2+}$.

A biosensor for $Hg^{2+}$ was prepared based on the regulatory gene merR from the mer resistance operon of a Serratia sp. This gene has been characterized by G. Nucifora et al., *J. Bacteriol.*, 171, 4241–4247, 1989. Mercury regulatory genes (merR) were obtained from S. Silver, University of Illinois, Urbana, Ill., in the form of a clone in the sequencing M13 phage, mGN2-220 or as a plasmid such as pDU1358 or pGN110. mGN2-220 has the following insert from pDU1358: merR, operator/-promoter: merT, merP, αmerA (FIG. 3). pGN110 has the following insert from pDU1358: merR, operator/promoter, merT, merP, merA, merB, ORF (FIG. 3).

The $Hg^{2+}$-responsive mercury biosensors were designed to contain the following portions of the mGN2-220 or pGN110 mer insert: merR, operator (O)/promoter (P), merT, αmerP (pCGLS201 and pJT207); merR, operator (O)/promoter (P), αmerT (pKL156); and merR, operator (O)/promoter (P), merT, merP merA (pKL152). The protocols followed were substantially those found in Maniatis et al. and the Promega *Applications Manual* cited above.

First, double stranded replicative form of mGN2-220 was prepared. Phage stock (100 µL, from S. Silver) was added to a 1:100 dilution into 500 mL Luria Broth (LB) of an overnight culture or *E. coli* DH5aF'I$^q$ grown in 3 mL of (LB) at 37 C. This culture was shaken vigorously at 37 C. for 6 to 8 hr. The culture was centrifuged at 10,000×g for 10 min to pellet the *E. coli*; the supernatant containing phage was discarded.

RF, which was amplified within the cells in the pellet, was obtained by a plasmid extraction procedure using known techniques. The pellet was resuspended in 25 mL of 20% sucrose, 100 mM Tris-HCl, pH 8.0, 20 mM EDTA (Solution 1) plus 2 mg/mL lysozyme suspended in 25 mL of the Solution 1. This was incubated at room temperature for 20 min. Freshly prepared 1% sodium dodecyl sulfate (SDS) (100 mL), 0.2M NaOH (Solution 2) was added to lyse the cells; the sample was incubated for an additional 0.5 hr at room temperature. 80 ml., of ice-cold 3M potassium acetate, pH 4.0 (Solution 3) was added to precipitate genomic DNA. After incubation for 1 hr at −20 C., the material was centrifuged at 10,000 ×g for 0.5 hr at 4 C.; the supernatant containing the RF was poured through cheesecloth into a fresh centrifuge bottle. An equal volume of cold 2-propanol was added, and mixed, after 10 min at room temperature, the sample was again centrifuged at 10,000 ×g for 0.5 hr to pellet the RF. The pellet was gently rinsed with 95% ethanol and then drained at least 15 min at room temperature to dry. Finally, the RF DNA was resuspended in 4 mL of 10 mM Tris-HCl, pH 8.0, 1 mM EDTA The RF was then purified by banding in CsCl by isopycnic density centrifugation. To the 4 mL sample was added precisely 4 g of CsCl plus 400 µL of a 10 mg/mL ethidium bromide solution. The sample was loaded into appropriate sample tubes for centrifugation in a Beckman VT165.1 or Sorvall TV-1665 vertical centrifuge rotor, or equivalent rotor, for 16 hr at 55,000 rpm at 15 C. Two bands are observed-the lower RF band was in the middle of the tube, and was removed with a syringe through an 18 gauge needle using known techniques. The ethidium bromide was removed from the RF DNA by extraction with an equal volume of 2-propanol saturated with TE and NaCl; the upper layer (2-propanol) turns pink and was discarded. 2-Propanol extraction was repeated until color was no longer observed in the upper phase; two additional extractions with 2-propanol are then completed. The CsCl was removed from the sample by either: 1) dialysis against 3 to 4 changes of TE for 24 hr, followed by addition of 0.1 volume of 3M sodium acetate and precipitation with two volumes of ethanol at 4 C. or at room temperature, or 2) by precipitating the RF DNA after increasing the volume three fold with distilled water and adding sixfold ethanol at 4 C. or room temperature, resuspending the precipitated DNA in 5 mL of TE, then repeating the precipitation by addition of 0.1 volume of 3M sodium acetate and precipitation with two volumes of ethanol at 4 C. or at room temperature. The DNA was brought up in 1 to 5 mL of TE and the DNA concentration determined by absorption spectroscopy.

RF was double digested with restriction endonucleases to obtain the desired mer operon fragment of approximately 1.4 Kb: merR, O/P, merT, merP. To 1 µg of DNA was added 1 µL of Hpa I and 1 µL of Sal I, 2 µL of 10× buffer (GIBCO/BRL REact® 4), and distilled water to make a final volume of 20 µL. The sample was incubated for 1 hr at 37 C. The completeness of the linearization/digestion was determined by electrophoresis in an 0.8% agarose gel in 1× TBE.

The 1.4 Kb fragment was then purified by electrophoresis in a preparative 0.8% agarose gel. The 1.4 Kb band was excised and extracted by freeze-squeeze using known techniques. The DNA was precipitated by addition of 0.1 volume of 3M sodium acetate and 2 volumes of ethanol. The DNA was resuspended in 1 mL of TE and the concentration determined by spectroscopy.

The 1.4 Kb mer operon fragment was next incorporated into appropriate lux cassette plasmids, such as pCGLS200, pJT204, or pJT205. The lux cassette plasmid was doubly cut with Sal I and Sma I using known techniques. 5 µg of the appropriate lux cassette plasmid was digested with 1 µL of Sal I (GIBCO/BRL), 2 µL of REact® 10, and the balance distilled water to make 20 µL total volume, for 1 hr at 37 C. The linearized lux cassette plasmid was precipitated with ethanol as described above, and resuspended in 17 µL of water. To this was added 2 µL of Sma I and 1 µL of REact® 4, and the DNA was digested for 1 hr at 37 C. Buffer and the small MCS fragment that was produced by digestion was removed by spin column (Select® D-50; 5'-3', Inc., Boulder, Colo.) using known techniques. The eluted DNA was precipitated with ethanol as described and resuspended in 10 µL of distilled water.

This lux cassette plasmid DNA was now ready to incorporate by ligation, in a directed fashion, the 1.4 Kb mer DNA. The blunt ended Hpa I and Sma I sites will specifically ligate, and the sticky end Sal I sites will specifically ligate. The transcriptional orientation of the mer DNA will be in the same direction as the transcriptional orientation of the lux operon DNA; the result was a transcriptional fusion of merR, O/P, merT, merP and promoterless lux (see FIG. 3).

Figure 5:
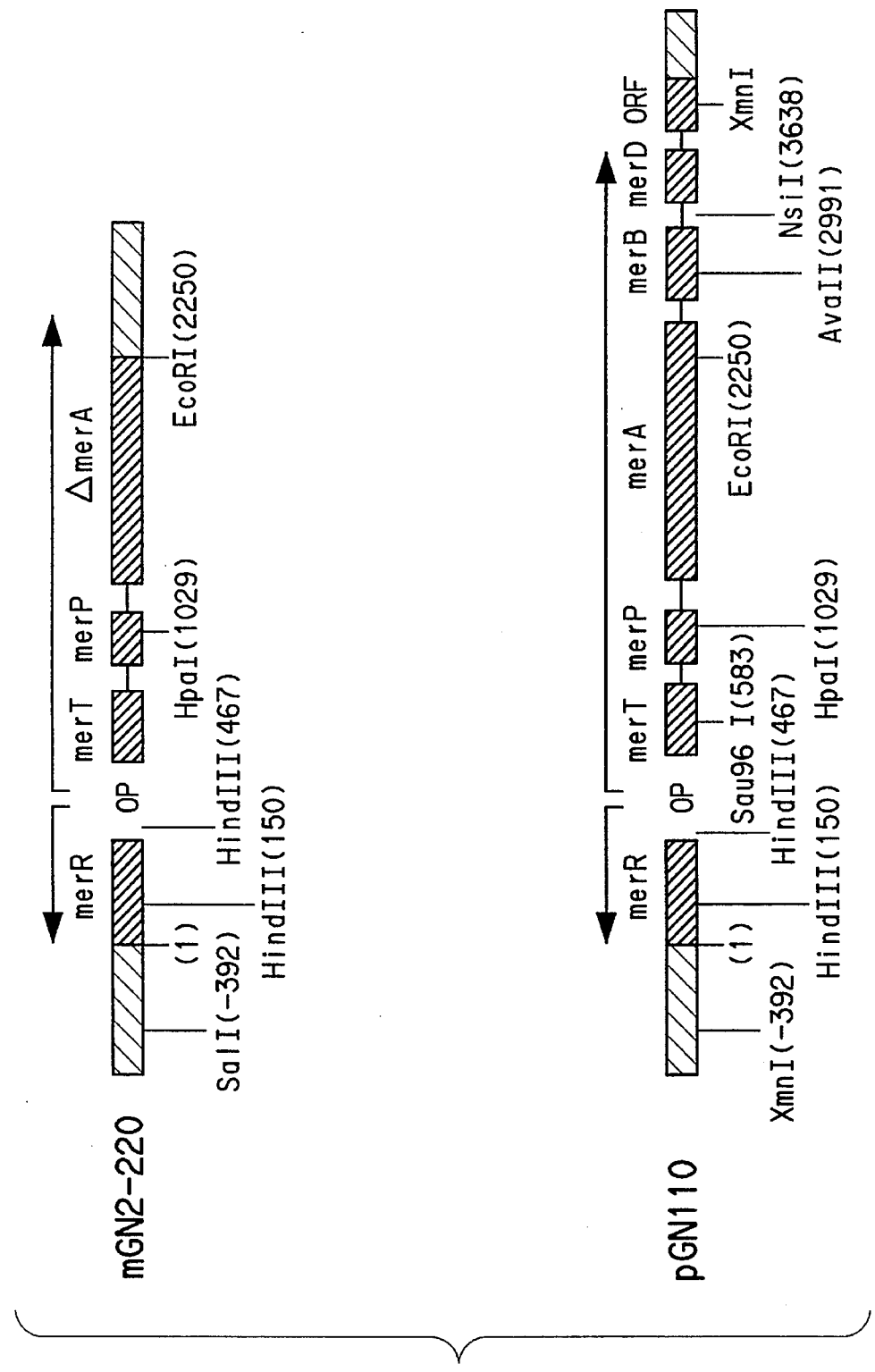
FIG. 5 Mercury genes used to engineer $Hg^{2+}$ and monomethyl mercury specific biosensors. These genes were originally from the *Serratia marcescens* plasmid, pDU1358. A restriction map of mer regulatory element of RF mGN2-220 and of the plasmid pGN110. Arrows indicate direction of transcription.
Figure 6:
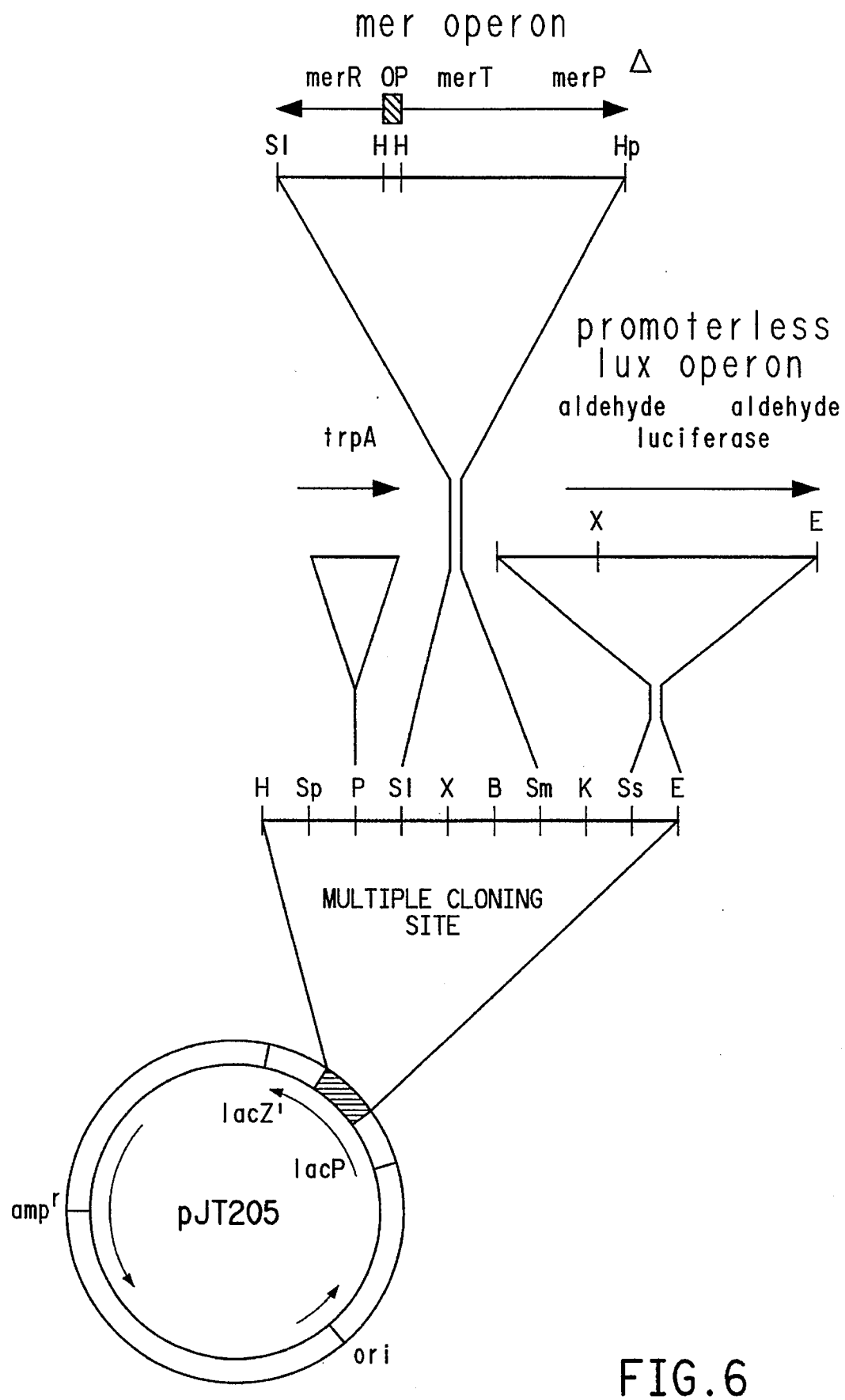
FIG. 6 A typical mer::lux fusion plasmid. A schematic of pJT207 where a 1.4 Kb Sal I/Hpa I mer fragment was incorporated into the lux cassette plasmid, pJT205.

Ligation was achieved by mixing 5 µL of the mer 1.4 Kb fragment, 2 µL of pCGLS200, pJT204, or pJT205, 5 µL of 5× ligase buffer, 1 µL of T4 DNA ligase ("GIBCO/BRL"), at 4 C. for 4 to 24 hr. The ligation mixture was added to 0.2 mL of competent *E. coli* such as strain LE392 or strain HB101 (competent cells are prepared as previously described), and the mixture was heat shocked and 0.02 mL and 1.8 mL plated onto LB plus ampicillin plates using known techniques. The plates are incubated overnight at 35 C. Colonies are checked for low level of light production and for a luminescent response to mercury; those clones that meet these criteria are biosensors for mercury.

pJT206 and pJT207 (Table 5) were prepared in a fashion similar to pCGLS201, with the exception that the lux cassette plasmids pJT204 and pJT205, respectively, were substituted for pCGLS200. All steps were otherwise the same.

pKL156 (Table 5) was prepared from the mer insert in pGN110 (FIG. 5) and the lux cassette plasmid pRPB78. The mer insert from plasmid pDU1358 had been inserted into the unique Sca I site of pBR322, creating pGN110. In the process of that cloning, upstream DNA 5' to the mer operon and 3' to merR was deleted (the Sal I site just upstream of the mer operon was destroyed); ligation created a new Xmn I site (originally an EcoR I site) 3' to merD (see FIG. 5). Xnm I cuts twice in the plasmid (once just upstream of the mer operon) and once just downstream of merD in the insert (FIG. 5). The mer operon can be completely removed from the plasmid, therefore, with Xmn I digestion. Specifically, 1 µg of preferably CsCl-purified pGN110 plasmid DNA prepared by known methods, was treated with 1 µL of Xmn I (New England BioLabs, Beverly, Mass.), 2 µL of 10× buffer (New England BioLabs Xmn I buffer), and distilled water to make a final volume of 20 µL. The sample was incubated for 1 hr at 37 C. The completeness of the linearization/digestion was determined by electrophoresis in an 0.8% agarose gel in 1× TBE.

The largest DNA fragment of 5.5 kb was purified by electrophoresis in a preparative 0.8% agarose gel. The 5.5 kb band was excised and extracted by freeze-squeeze using known techniques. The DNA was precipitated by addition of 0.1 volume of 3M sodium acetate and 2 volumes of ethanol. The DNA was resuspended in 1 mL of TE and the concentration determined by spectroscopy.

1 µg of the 5.5 kb fragment was then digested with 1 µL of Eco47 III, 2 µL of 10× REact® 6 (GIBCO/BRL), and distilled water to make a final volume of 20 µL. The sample was incubated for 1 hr at 37 C. The reaction mixture was then subjected to gel electrophoresis in an 0.8% agarose gel in 1× TBE, and the 2 kb band selected, excised and precipitated as described immediately above.

The 2 kb fragment was then ligated into pRPB78 linearized with Sma I using standard techniques already described. The resulting plasmid was transformed into *E. coli* LE392 as described above, creating the mercury plasmid pKL156.

pKL152 was created in a fashion similar to pKL156. The 5.5 kb mer fragment from pGN110 described immediately above, was digested with 1 µL of Ava II (cuts near the 5' end of merB), 2 µL of 10× REact® 6 (GIBCO/BRL) and distilled water to make a final volume of 20 µL. The sample was incubated for 1 hr at 37 C. The reaction mixture was then subjected to gel electrophoresis in an 0.8% agarose gel in 1× TBE, and the larger of two bands, a 3.7 kb band, was selected, excised and precipitated as described above. The fragment ends were filled-in with Klenow and dNTPs and ligated into pJT205 linearized with Sma I as described above, creating the mercury plasmid pKL152.

EXAMPLE 5

This example illustrates a biosensor that responds specifically to $Hg^{2+}$ and to monomethyl mercury by producing light proportional to the mercury concentration.

A biosensor for $Hg^{2+}$ and monomethyl mercury was prepared based on the regulatory gene merR from the mer resistance operon of a Serratia sp. This gene has been characterized by G. Nucifora et al., *J. Bacteriol.*, 171, 4241–4247, 1989. Mercury regulatory genes (merR) were obtained from S. Silver, University of Illinois, Urbana, Ill., in the form of a plasmid such as pDU1358 or pGN110. pGN110 has the following insert from pDU1358: merR, operator/promoter, merT, merP, merA, merB, ORF (FIG. 3).

The $Hg^{2+}$ and monomethyl mercury-responsive mercury biosensors were designed to contain the following portions of the pGN110 mer insert: merR, operator (O)/promoter (P), merT, merP merA merB (pKL48). The protocols followed were substantially those found in Maniatis et al. and the Promega *Applications Mammal* cited above.

The 5.5 kb mer fragment from pGN110 (see section above) was digested with 1 µL of Nsi I (which cuts in the intergenic space between merB and merD), 2 µL of 10× REact® 6 (GIBCO/BRL) and distilled water to make a final volume of 20 µL. The sample was incubated for 1 hr at 37 C. The reaction mixture was then subjected to gel electrophoresis in an 0.8% agarose gel in 1× TBE, and the larger of the two bands, a 4.4 kb band, was selected, excised and precipitated as described above. The fragment ends were filled-in with Klenow and dNTPs and ligated into pJT205 linearized with Sma I as described above, creating the mercury ligated into pJT205 linearized with Sma I as described above, creating the mercury plasmid pKL48.

EXAMPLE 6

This example demonstrates the luminescent response of mercury biosensors.

Figure 7:
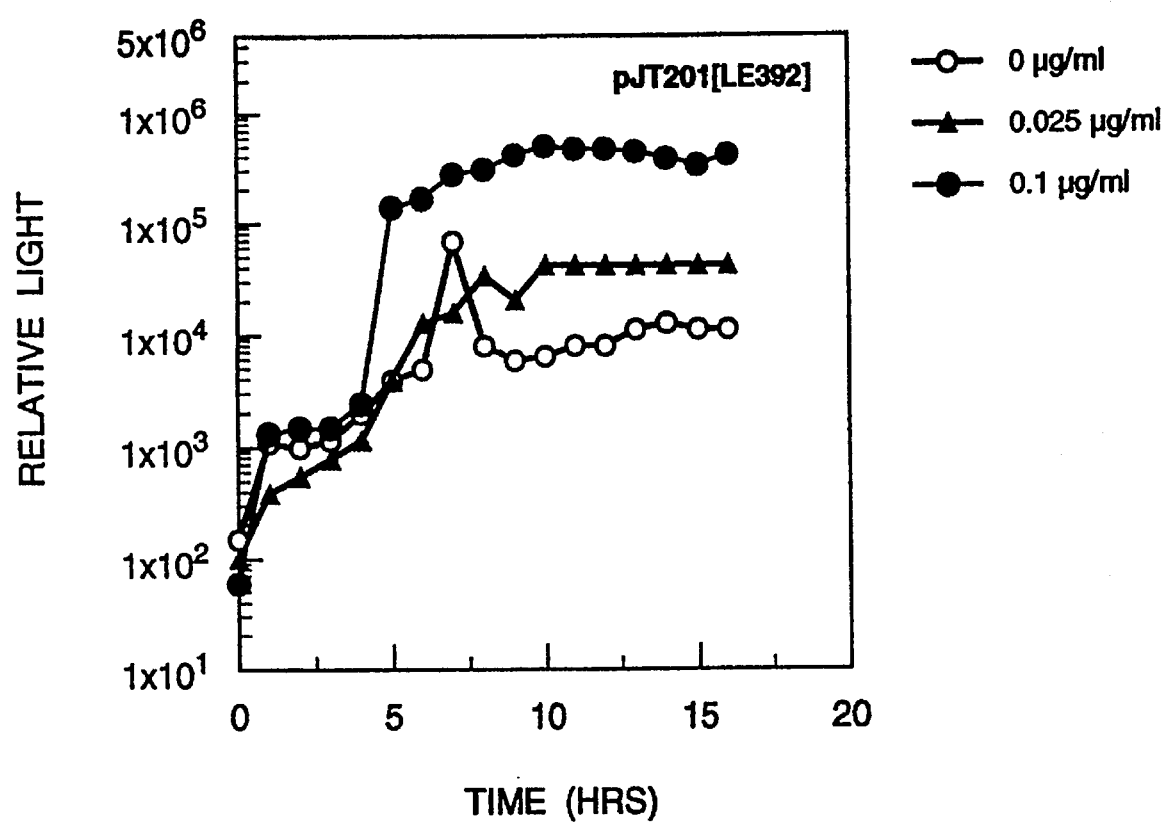
FIG. 7 Luminescent response of pJT201 in *E. coli* LE392 to $HgCl_2$ present during growth in LB-AMP at 30 C.

Luminescence of the biosensors was measured on a Pacific Photometrics Lab Photometer or amplifier/voltmeter with output from a photomultiplier tube or photodiode photometer of this invention as previously described or equivalent. Cell density was reported as optical density (OD) at 600 nm. Relative background luminescence levels of representative clones are summarized in Table 5. The luminescent response of pCGLS201 [LE392] (plasmid pCGLS201 transformed into *E. coli* LE392) during growth with and without 0.025 and 0.1 µg/mL $Hg^{2+}$ was shown in FIG. 7. Since this lux cassette plasmid still retains natural promoter activity, the background luminescence increased significantly over the course of the incubation period. A measurable response of about 1.5 fold over background was seen with 0.025 µg/mL $Hg^{2+}$, a 17 fold response over background was observed with 0.1 µg/mL $Hg^{2+}$ (FIG. 7).

Figure 8:
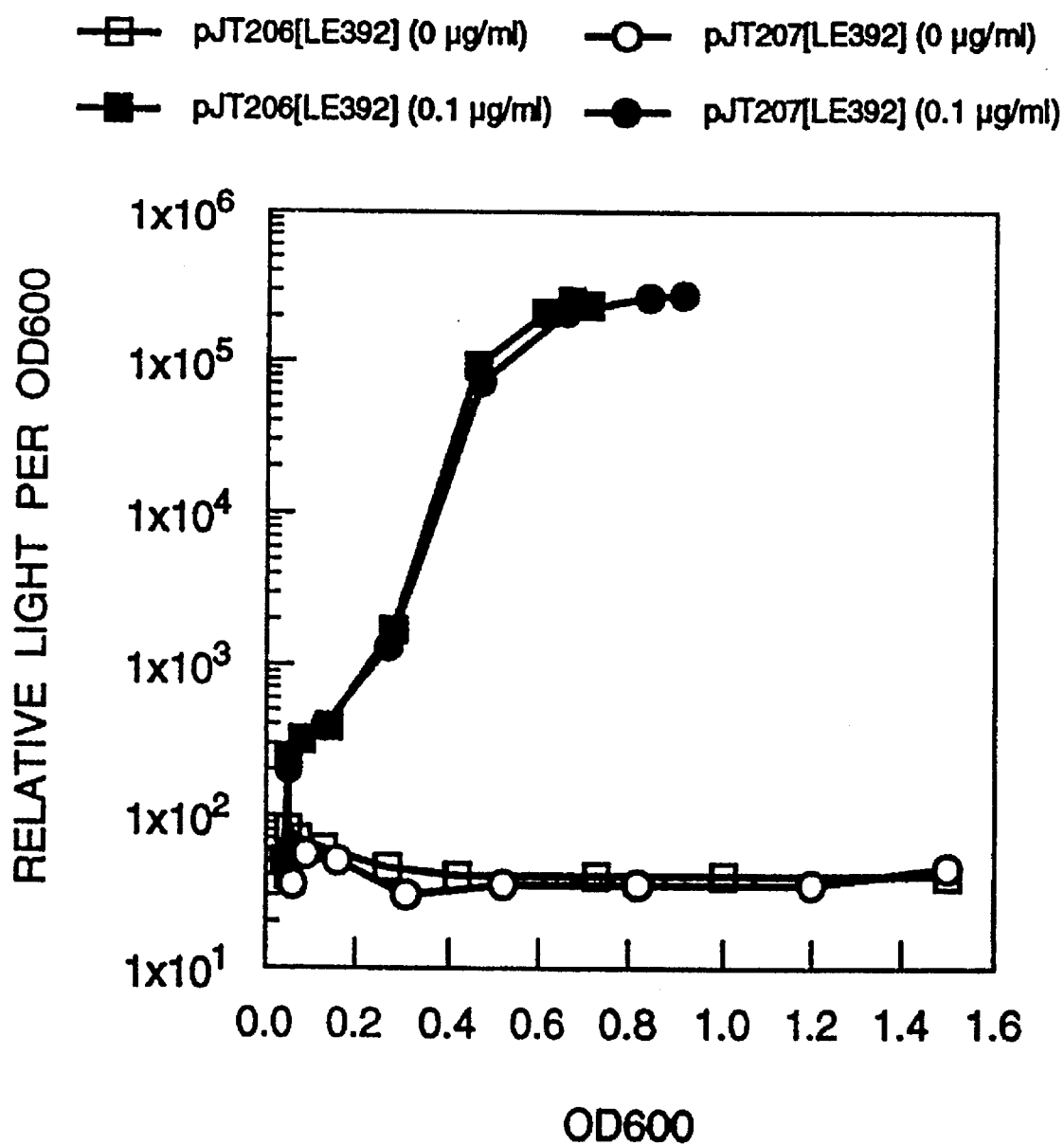
FIG. 8 Luminescent response of pJT206 and pJT207 in *E. coli* LE392 to $HgCl_2$ present during growth in LB-AMP at 30 C.

Better response was noted with pJT206[LE392] and pJT207[LE392]. These mercury biosensors had substantially lower background luminescence levels and a 5,000 fold response over background to mercury (FIG. 8). This was primarily due to the low background luminescence (in the absence of mercury) resulting from deletion of the natural promoter of the *X. luminescens* lux operon.

Figure 9:
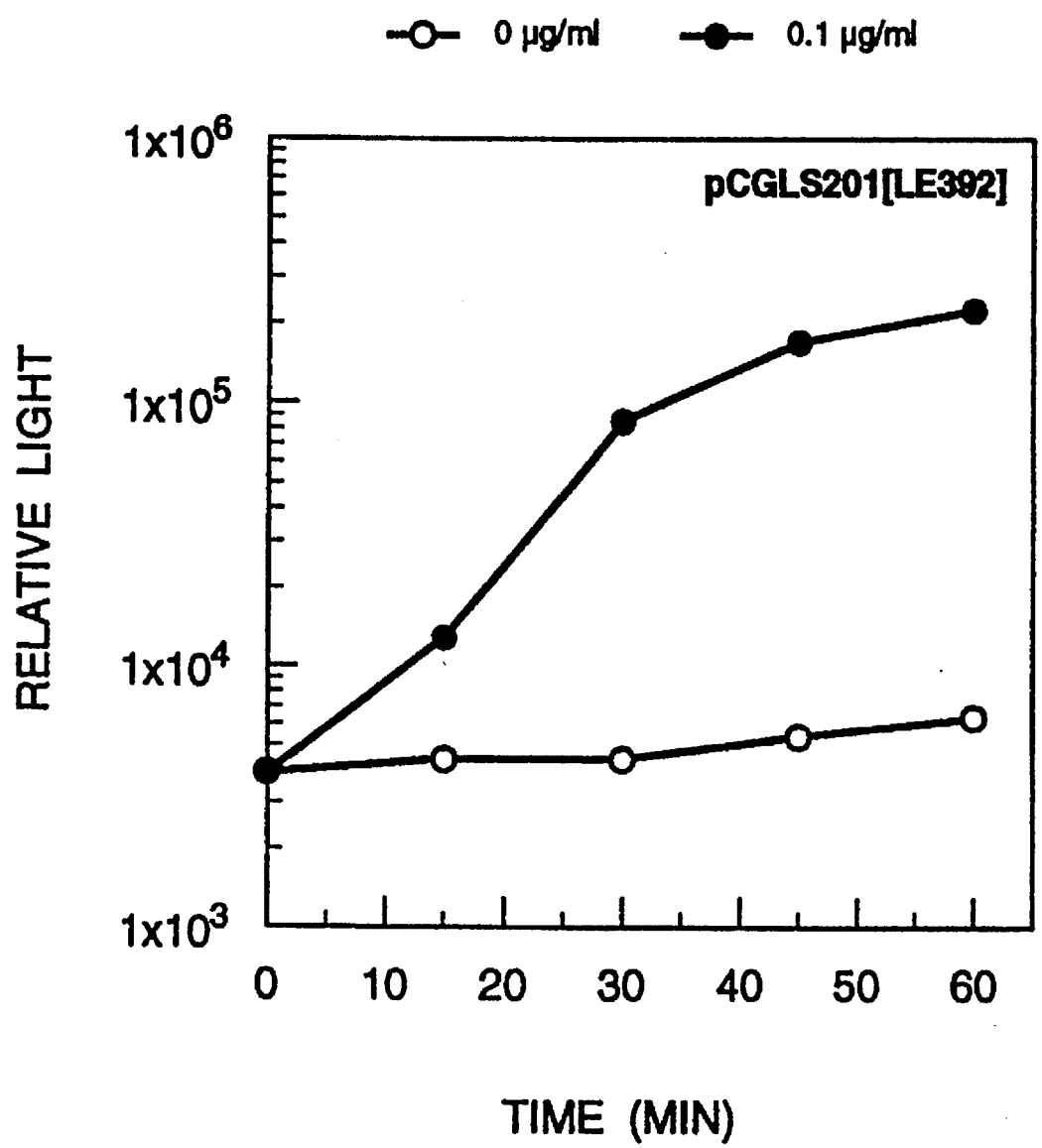
FIG. 9 Rapid luminescent response of pJT201 in *E. coli* LE392 suspended in LB-AMP to $HgCl_2$. Cultures were grown in LB-AMP for 6 hours at 30 C., then transferred to fresh LB-AMP with and without $HgCl_2$.
Figure 10:
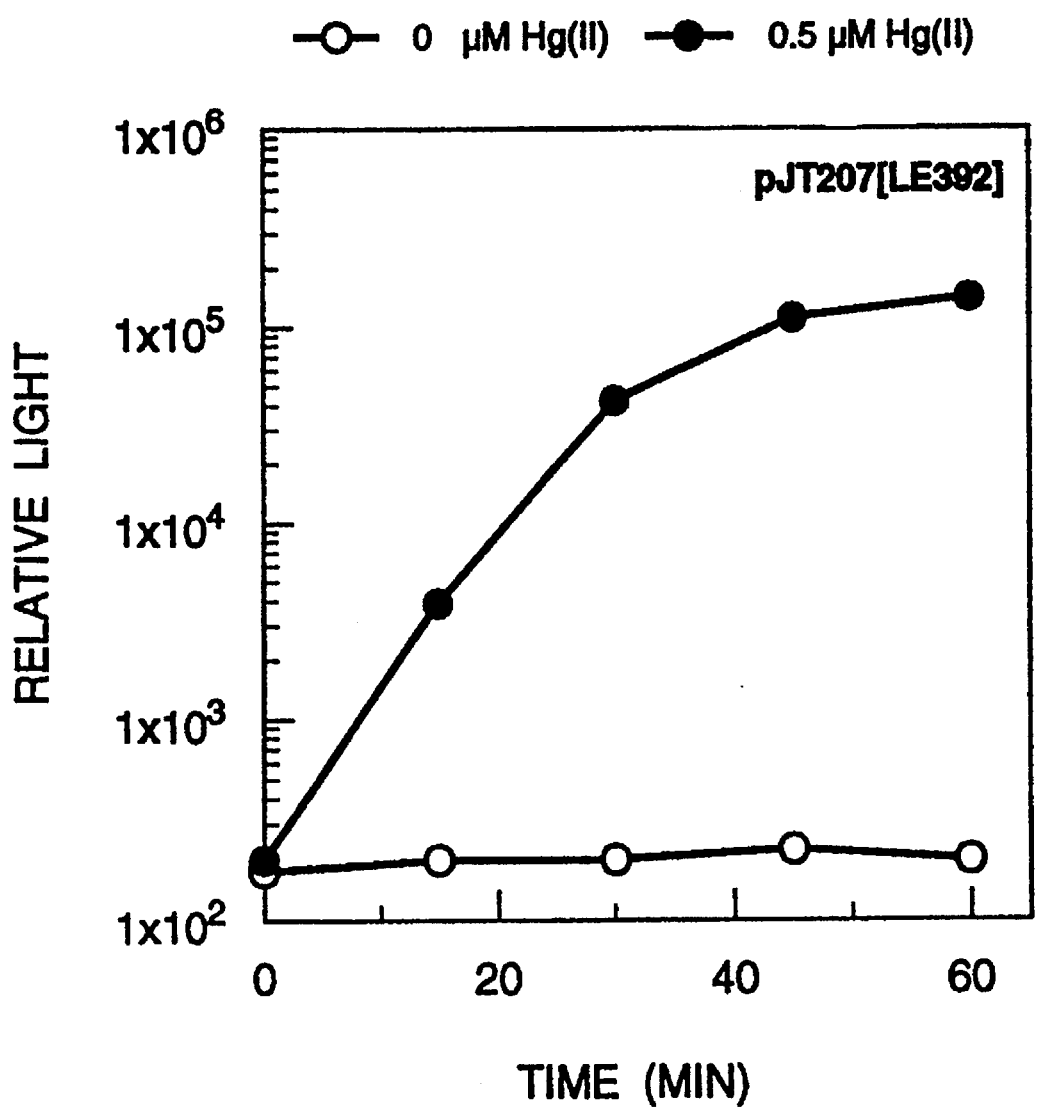
FIG. 10 Rapid luminescent response of pJT207 in *E. coli* LE392 suspended in LB-AMP to $HgCl_2$. Cultures were grown in LB-AMP for 6 hours at 30 C., then transferred to fresh LB-AMP with and without $HgCl_2$.

Rapid response tests to $Hg^{2+}$ demonstrated that these biosensors were sensitive and responsive (see FIG. 9). The kinetics of the pCGLS201 biosensor to 0.1 µg $Hg^{2+}$ shows the luminescent response for 4 to 6 hr mid-exponential phase growth cells was easily measurable within 15 min, was 80% of maximum within 0.5 hr, and was essentially complete within 1 hr (FIG. 9). One hour rapid response to $Hg^{2+}$ of cells taken at 2, 4, 6, and 8 hr of growth indicates that 4 to 8 hr cells are desirable when *E. coli* LE392 was the host carrier.

pJT205 and pJT206, with promoterless lux, had even lower background luminescence levels than pJT201 (FIG. 10). The 1 hr luminescent response to 0.5 µM $Hg^{2+}$ was 1000 fold over background. As with pCGLS201, 4 to 8 hr cells are desirable when E. coli LE392 was the host carrier.

Figure 11:
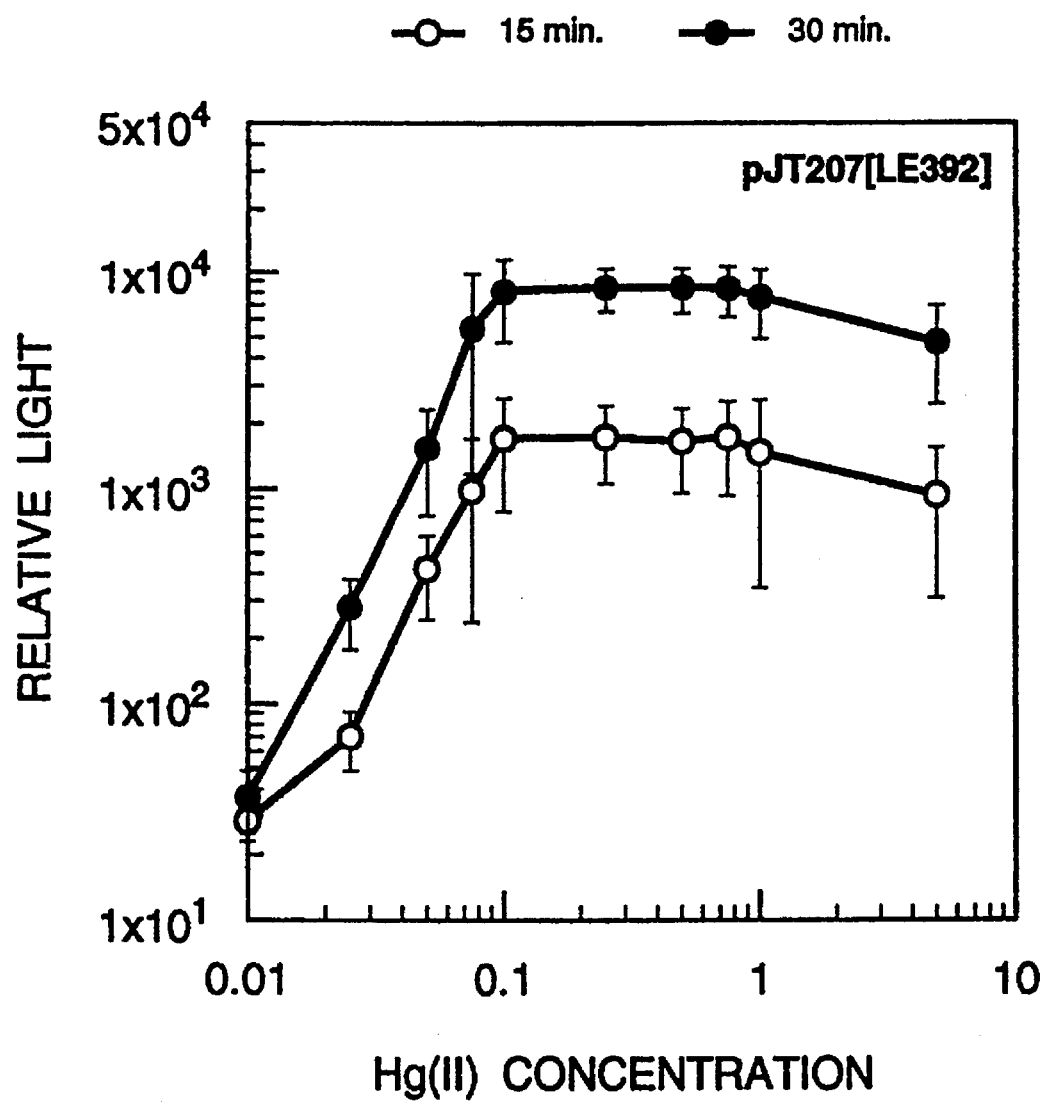
FIG. 11 Rapid luminescent response of pJT207 in *E. coli* LE392 suspended in LB-AMP to a range of $HgCl_2$ concentrations. Cultures were grown in LB-AMP for 6 hours at 30 C., then transferred to fresh LB-AMP with and without $HgCl_2$.
Figure 12:
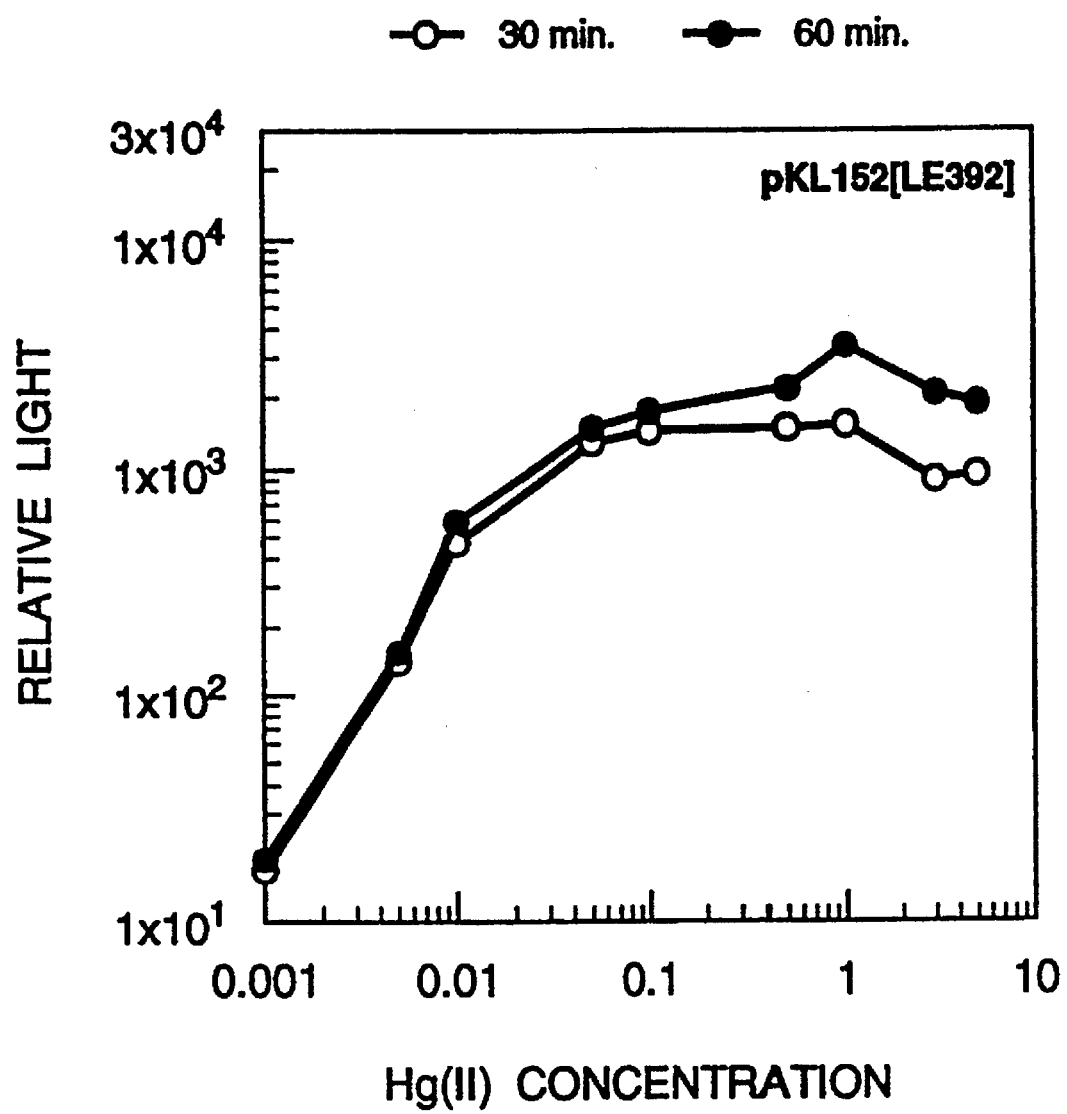
FIG. 12 Rapid luminescent response of pKL152 in *E. coli* LE392 suspended in LB-AMP to a range of $HgCl_2$ concentrations. Cultures were grown in LB-AMP for 6 hours at 30 C., then transferred to fresh LB-AMP with and without $HgCl_2$.
Figure 13:
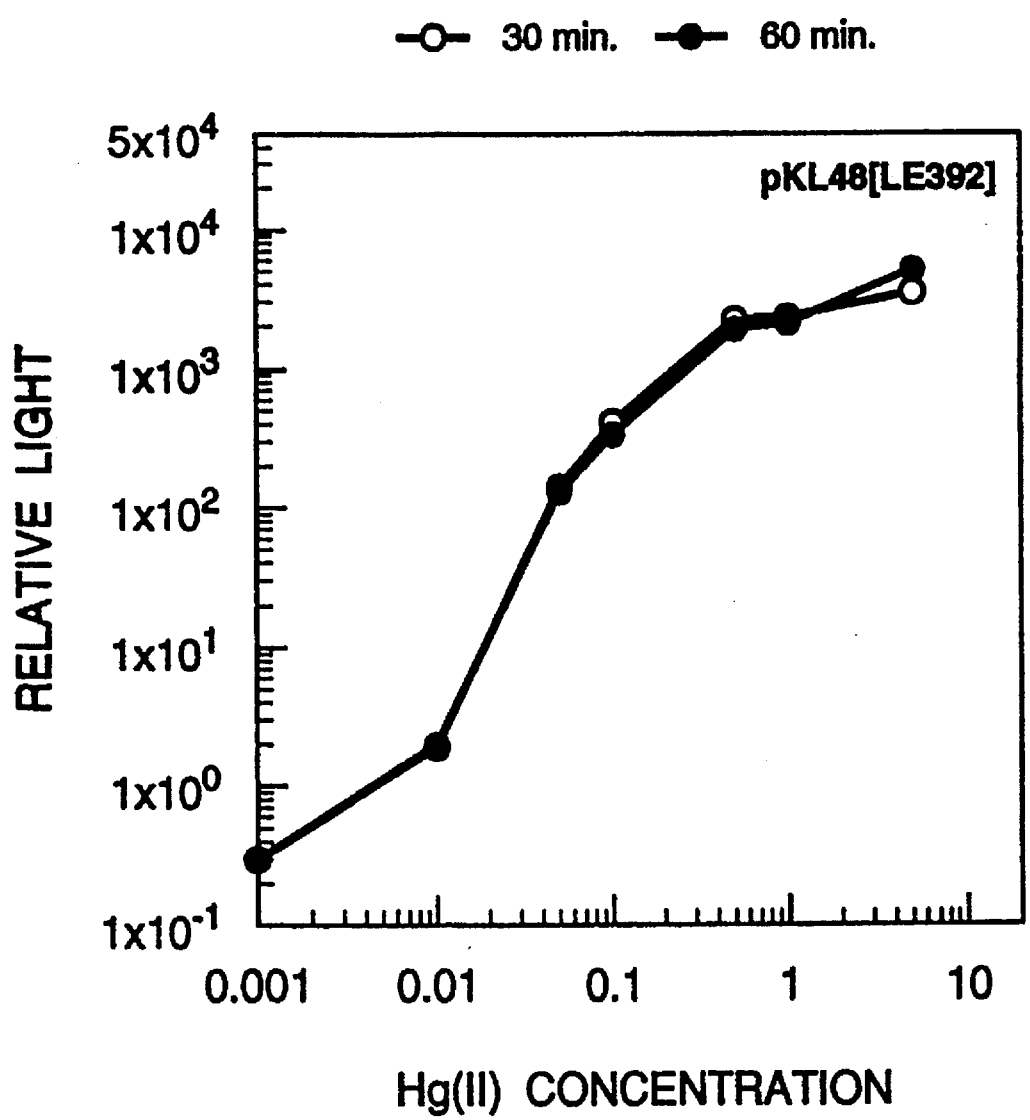
FIG. 13 Rapid luminescent response of pKL48 in *E. coli* LE392 suspended in LB-AMP to a range of $HgCl_2$ concentrations. Cultures were grown in LB-AMP for 6 hours at 30 C., then transferred to fresh LB-AMP with and without $HgCl_2$.

The luminescent response of mercury biosensors with partial mercury transport (pJT207; FIG. 11), with full mercury transport and specific resistance (pKL152, FIG. 12; and pKL48, FIG. 13) to $Hg^{2+}$ was similar. The proportional response range was slightly different for each construct: pJT207, 0.01 to 0.1 µM $Hg^{2+}$; pKL152, 0.001 to 0.1 µM $Hg^{2+}$; and pKL48, 0.001 to 1 µM $Hg^{2+}$. It was notable that the hypersensitive (in terms of $Hg^{2+}$ toxicity to growth) mercury biosensor, pJT207, was not the most hyperresponsive construct. The most responsive construct, pKL48, had the lowest background luminescence and the greatest range of response. This is a significant improvement over previously reported mercury biosensors.

Figure 14:
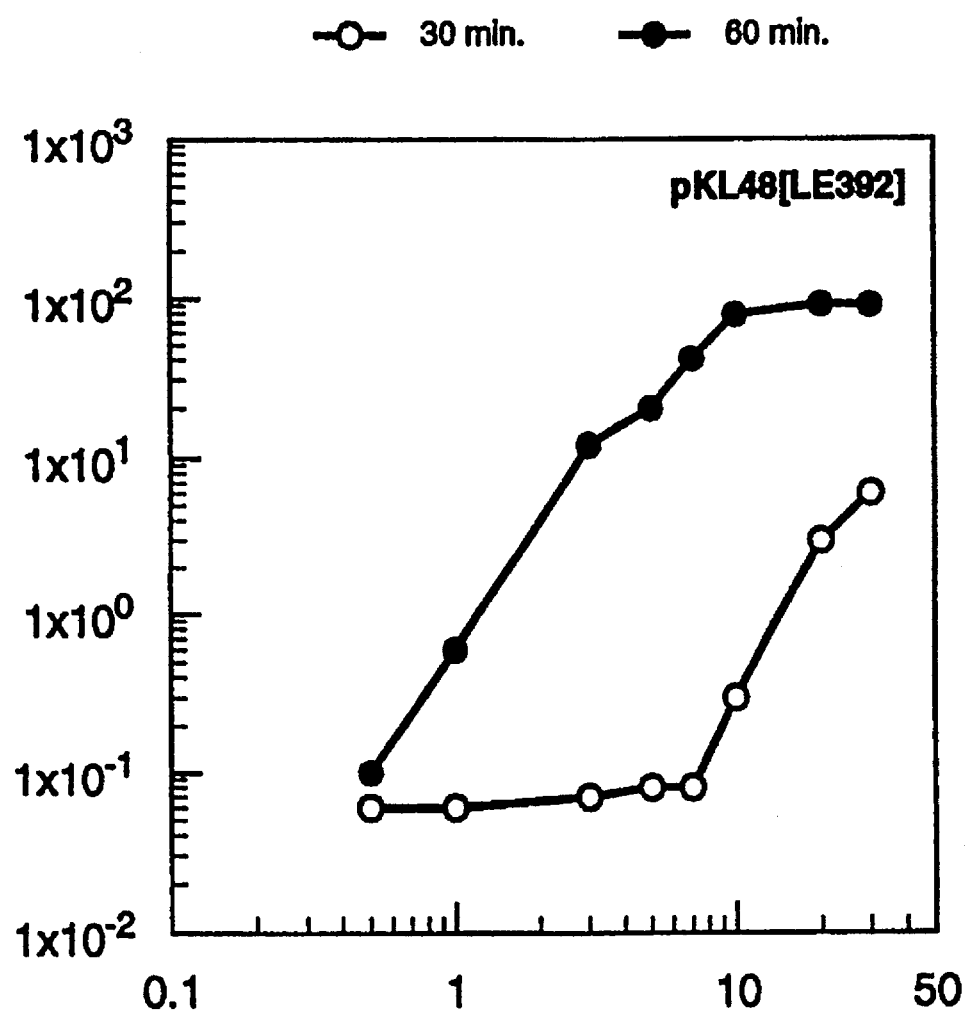
FIG. 14 Rapid luminescent response of pKL48 in *E. coli* LE392 suspended in M9+glycerol+1 mM cysteine to a range of monomethyl mercury concentrations. Cultures were grown in LB-AMP for 6 hours at 30 C., then transferred to fresh M9+glycerol+1 mM cysteine with and without monomethyl mercury.

Only pKL48 responded to monomethyl mercury (FIG. 14). This results from the presence of merB and the merB gene product, organomercury lyase. A proportional response was noted between 0.5 and 10 µM monomethyl mercury.

---

What is claimed is:

1. A device for the detection of mercury in water comprising:
   (1) an aqueous suspension of biosensory microorganism cells, the microorganism cells containing a recombinant plasmid, the recombinant plasmid comprising a plasmid cassette, the plasmid cassette comprising:
      (a) a promoterless, lux gene operon complex from *Xenorhabdus luminescens*, the lux operon complex comprising luxC, luxD, luxA, luxB, and luxE genes; and
      (b) an inducible regulatory gene that is activated by exposure to divalent mercury ions, the regulatory gene being located 5' of the lux gene operon complex; and
   (2) a receptacle, the aqueous suspension being present in the receptacle;
   (3) a light-tight container, the receptacle being present in the container; and
   (4) means for detecting bioluminescence operably connected to the aqueous suspension of biosensory microorganism cells by a means for conveying bioluminescence.

2. The device of claim 1 wherein the microorganisms are *Escherichia coli*.

3. The device of claim 1 wherein the recombinant plasmid additionally comprises an antibiotic resistance gene and a transcription terminator located 5' to both the lux gene operon complex and the inducible regulatory gene.

4. The device of claim 1 wherein the means for detecting bioluminescence is photographic film.

5. The device of claim 1 wherein the means for detecting bioluminescence is a photomultiplier.

6. The device of claim 1 wherein the means for detecting bioluminescence is a photodiode photometer.

7. A device for the detection of mercury and for the detection of monomethyl mercury in water comprising:
   (1) an aqueous suspension of biosensory microorganism cells, the microorganism cells containing a recombinant plasmid, the recombinant plasmid comprising a plasmid cassette, the plasmid cassette comprising:
      (a) a promoterless, lux gene operon complex from *Xenorhabdus luminescens*, the lux operon complex comprising luxC, luxD, luxA, luxB, and luxE genes; and
      (b) an inducible regulatory gene that is activated by exposure to divalent mercury ions and by exposure to monomethyl mercury, the regulatory gene being located 5' of the lux gene operon complex; and
   (2) a receptacle, the aqueous suspension being present in the receptacle;

(3) a light-tight container, the receptacle being present in the container; and (4) means for detecting bioluminescence operably connected to the aqueous suspension of biosensory microorganism cells by a means for conveying bioluminescence.

8. The device of claim 7 wherein the microorganisms are *Escherichia coli*.

9. The device of claim 7 wherein the recombinant plasmid additionally comprises an antibiotic resistance gene and a transcription terminator located 5' to both the lux gene operon complex and the inducible regulatory gene.

10. The device of claim 7 wherein the means for detecting bioluminescence is photographic film.

11. The device of claim 7 wherein the means for detecting bioluminescence is a photomultiplier.

12. The device of claim 7 wherein the means for detecting bioluminescence is a photodiode photometer.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 506 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CTGCAGCCCG  GTACCGAGCT  CGAATTCTTC  TTTAGAAATC  TGCCGGTAAA  AATTAGATTG    60
CTATTCAATC  TATTTCTATC  GGTATTTGTG  AAATAATACT  CAGGATAATA  ATTTACATAA   120
ATATTATCAC  GCATTAGAGA  AGAGCATGAC  TTTTTTAATT  TAAACTTTTC  ATTAACAAAT   180
CTTGTTGATA  TGAAAATTTT  CCTTTGCTAT  TTTAACAGAT  ATTAAAACGG  GAATAGGCGT   240
TATATTGACG  ATCCATTCAG  TTAGATTAAA  AACCTTGAGC  AGAAAATTTA  TATTATTATC   300
ATAATTATGA  CGAAAGTTAC  AGGCCAGGAA  CCACGTAGTC  AGAATCTGAT  TTTCTATATA   360
TTTGTTATTT  ACATCGTCAT  AACACAAAAA  TATAAGAAGC  AAGTGTTGGT  ACGACCAGTT   420
CGCAAGTAAG  TTAACGCACT  TAGTGAATAC  CCATTAATGG  ATGGCAATAT  GACTAAAAAT   480
TCATCATATC  GCAGTGAATC  TTCCGA                                           506
```

( 2 ) INFORMATION FOR SEQ ID NO:2:

( i ) SEQUENCE CHARACTERISTICS:
        ( A ) LENGTH: 476 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CTGCAGCCCG  GGTACCGAGC  TCGCGCCATT  CAGGCTGCGC  AACTGTTGGG  GCAAATATGA    60
CTAAAAAAT   TTCATTCATT  ATTAACGGCC  AGGTTGAAAT  CTTTCCCGAA  AGTGATGATT   120
TAGTGCAATC  CATTAATTTT  GGTGATAATA  GTGTTTACCT  GCCAATATTG  AATGACTCTC   180
ATGTAAAAAA  CATTATTGAT  TGTAATGGAA  ATAACGAATT  ACGGTTGCAT  AACATTGTCA   240
ATTTTCTCTA  TACGGTAGGG  CAAAGATGGA  AAAATGAAGA  ATACTCAAGA  CGCAGGACAT   300
ACATTCGTGA  CTTAAAAAAA  TATATGGGAT  ATTCAGAAGA  AATGGCTAAG  CTAGAGGCCA   360
ATTGGATATC  TATGATTTTA  TGTTCTAAGG  CGGCCTTATG  ATGTTGATGA  AATGACTTGG   420
TTCTCGCCAT  ATCATGGATG  ATGCTCATCA  GGATGAAGTT  ATGTTCGGCT  TTCGAA       476
```

( 2 ) INFORMATION FOR SEQ ID NO:3:

( i ) SEQUENCE CHARACTERISTICS:
        ( A ) LENGTH: 326 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| GGCAAATATG | ACTAAAAAAA | TTTCATTCAT | TATTAACGGC | CAGGTTGAAA | TCTTTCCCGA | 60 |
| AAGTGATGAT | TTAGTGCAAT | CCATTAATTT | TGGTGATAAT | AGTGTTACC | TGCCAATATT | 120 |
| GAATGACTCT | CATGTAAAAA | ACATTATTGA | TTGTAATGGA | AATAACGAAT | TACGGTTGCA | 180 |
| TAACATTGTC | AATTTTCTCT | ATACGGTAGG | GCAAAGATGG | AAAAATGAAG | AATACTCAAG | 240 |
| ACGCAGGACA | TACATTCGTG | ACTTAAAAAA | ATATATGGGA | TATTCAGAAG | AAATGGCTAA | 300 |
| GCTAGAGGCC | AATTGGATAT | CTATGA | | | | 326 |

( 2 ) INFORMATION FOR SEQ ID NO:4:

( i ) SEQUENCE CHARACTERISTICS:
        ( A ) LENGTH: 375 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
| CTGCAGCCCG | GGTACCGAGC | TCGCGCCATT | CAGGCTGCGC | AACTGTTGGG | GCAAATATGA | 60 |
| CTAAAAAAT | TTCATTCATT | ATTAACGGCC | AGGTTGAAAT | CTTTCCCGAA | AGTGATGATT | 120 |
| TAGTGCAATC | CATTAATTTT | GGTGATAATA | GTGTTACCT | GCCAATATTG | AATGACTCTC | 180 |
| ATGTAAAAA | CATTATTGAT | TGTAATGGAA | ATAACGAATT | ACGGTTGCAT | AACATTGTCA | 240 |
| ATTTTCTCTA | TACGGTAGGG | CAAAGATGGA | AAAATGAAGA | ATACTCAAGA | CGCAGGACAT | 300 |
| ACATTCGTGA | CTTAAAAAAA | TATATGGGAT | ATTCAGAAGA | AATGGCTAAG | CTAGAGGCCA | 360 |
| ATTGGATATC | TATGA | | | | | 375 |

( 2 ) INFORMATION FOR SEQ ID NO:5:

( i ) SEQUENCE CHARACTERISTICS:
        ( A ) LENGTH: 326 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | | |
|---|---|---|---|---|---|---|
| GGCAAATATG | ACTAAAAAAA | TTTCATTCAT | TATTAACGGC | CAGGTTGAAA | TCTTTCCCGA | 60 |
| AAGTGATGAT | TTAGTGCAAT | CCATTAATTT | TGGTGATAAT | AGTGTTACC | TGCCAATATT | 120 |
| GAATGACTCT | CATGTAAAAA | ACATTATTGA | TTGTAATGGA | AATAACGAAT | TACGGTTGCA | 180 |
| TAACATTGTC | AATTTTCTCT | ATACGGTAGG | GCAAAGATGG | AAAAATGAAG | AATACTCAAG | 240 |
| ACGCAGGACA | TACATTCGTG | ACTTAAAAAA | ATATATGGGA | TATTCAGAAG | AAATGGCTAA | 300 |
| GCTAGAGGCC | AATTGGATAT | CTATGA | | | | 326 |

( 2 ) INFORMATION FOR SEQ ID NO:6:

( i ) SEQUENCE CHARACTERISTICS:
      ( A ) LENGTH: 325 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
| GGCAAATATG | AACAAAAAAA | TTTCATTCAT | TATTAACGGT | CGAGTTGAAA | TATTTCCTGA | 60 |
| AAGTGATGAT | TTAGTGCAAT | CCATTAATTT | TGGTGATAAT | AGTGTTCATT | TGCCAGTATT | 120 |
| GAATGATTCT | CAAGTAAAAA | ACATTATTGA | TTATAATGAA | AATAATGAAT | TGCAATTGCA | 180 |
| TAACATTATC | AACTTTCTCT | ATACGGTAGG | GCAACGATGG | AAAAATGAAG | AATATTCAAG | 240 |
| ACGCAGGACA | TATATTCGTG | ATCTAAAAAG | ATATATGGGA | TATTCAGAAG | AAATGGCTAG | 300 |
| CTAGAGGCCA | ACTGGATATC | TATGA | | | | 325 |

( 2 ) INFORMATION FOR SEQ ID NO:7:

( i ) SEQUENCE CHARACTERISTICS:
      ( A ) LENGTH: 326 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:7:

| | | | | | | |
|---|---|---|---|---|---|---|
| GGCAAATATG | CCACCAAAAA | TTTCATTCAT | TATTAACGGT | CGAGTTGAAA | TATTTCCTGA | 60 |
| AAGTGATGAT | TTAGTGCAAT | CCATTAATTT | TGGTGATAAT | AGTGTTCATT | TGCCAGTATT | 120 |
| GAATGATTCT | CAAGTAAAAA | ACATTATTGA | TTATAATGAA | AATAATGAAT | TGCAATTGCA | 180 |
| TAACATTATC | AACTTTCTCT | ATACGGTAGG | GCAACGATGG | AAAAATGAAG | AATATTCAAG | 240 |
| ACGCAGACCA | TATATTCGTG | ATCCTAAAAA | GATATATGGG | ATATTCAGAA | GAATGGCTAA | 300 |
| GCTAGAGGCC | AATCGGATAT | CTATGA | | | | 326 |